(12) United States Patent
Schwartz et al.

(10) Patent No.: US 7,442,681 B2
(45) Date of Patent: Oct. 28, 2008

(54) METHOD OF INHIBITING VASCULAR PERMEABILITY

(75) Inventors: Martin A. Schwartz, Earlysville, VA (US); Rebecca A. Stockton, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 349 days.

(21) Appl. No.: 11/054,789

(22) Filed: Feb. 10, 2005

(65) Prior Publication Data

US 2005/0233965 A1  Oct. 20, 2005

Related U.S. Application Data

(60) Provisional application No. 60/543,337, filed on Feb. 10, 2004.

(51) Int. Cl.
*A61K 38/00* (2006.01)
*C07K 17/00* (2006.01)
*C12Q 1/06* (2006.01)

(52) U.S. Cl. .............................. 514/2; 514/12; 530/350; 530/324; 435/39; 435/810

(58) Field of Classification Search ...................... 514/2, 514/12; 530/350, 324; 435/39, 810
See application file for complete search history.

(56) References Cited

U.S. PATENT DOCUMENTS

| 6,248,549 B1 * | 6/2001 | Van Eyk et al. ............... 435/15 |
| 2004/0138133 A1 | 7/2004 | Cheresh et al. | |

OTHER PUBLICATIONS

Kiosses et al. A Role for p21-Activated Kinase in Endothelial Cell Migration, Nov. 15, 1999, The Journal of Cell Biology, vol. 147, No. 4, pp. 831-843.*
Dudek et al. Cytoskeletal regulation of pulmonary vascular permeability, 2002, J. Appl. Physiol., vol. 91, pp. 1487-1500.*
Galisteo et al. The Adaptor Protein Nck Links Receptor Tyrosine Kinase with the Serine-Threonine Kinase Pak1, Aug. 30, 1996, The Journal of Biological Chemistry, vol. 271, No. 35, pp. 20997-21000.*
Bokoch et al. Interaction of the Nck Adapter Protein with p21-activated Kinase (PAK), Oct. 18, 1996, The Journal of Biological Chemistry, vol. 217, No. 42, pp. 25746-25749.*
Schwarze et al. In Vivo Protein Transduction: Delivery of a Biologically Active Protein into the Mouse, Sep. 3, 1999, Science, vol. 285, pp. 1569-1572.*
Kioses, W.B., et al., "A Dominant-Negative p65 PAK Peptide Inhibits Angiogenesis", Circulation Research, 2002, vol. 90(6), pp. 697-702.
Stockton, R.A., et al., "p21-activated Kinase Regulates Endothelial Permeability through Modulation of Contractility", The Journal of Biological Chemistry, 2004, vol. 45(5), pp. 46621-46630.
Gute, D.C., et. al., "Inflammatory Responses to ischemia and reperfusion in skeletal muscle," Mol Cell Biochem, vol. 179 ( No. 1-2), p. 169-87, (1998).
Edwards, S.L., "Tissue viability: understanding the mechanisms of injury and repair," Nurs Stand, vol. 21 (13), p. 48-56; quiz 58, (2006).
Paul, R., et. al., "Src deficiency or blockade of Src activity in mice provides cerebral protection following stroke", Nat. Med., vol. 7, p. 222-227 (2001).
Weis, S., et. al., "Src blockade stabilizes a Flk/cadherin complex, reducing edema and tissue injury following myocardial infarction", J. Clin. Invest., vol. 113, p. 885-894, (2004).
Orfanos, S.E., et. al., "Pulmonary endothelium in acute lung injury: from basic science to the critically ill", Intensive Care Med., vol. 30(9), p. 1702-14, (2004).
Esper, A.M., et. al., "Evolution of treatments for patients with acute lung injury", Expert Opin. Investig. Drugs, vol. 14(5), p. 633-45, (2005).
Marx, G., "Fluid therapy in sepsis with capillary leakage", Eur. J. Anaesthesiol., vol. 20(6), p. 429-42 (2003).
Demling, R.H., "The burn edema process: current concepts", J. Burn Care Rehabil., vol. 26(3), p. 207-27, (2005).
Taber's Cyclopedic Medical Dictionary, Edition 20, pp. 118, 1640, 2005.
Murohara, T., et. al., "Vascular Endothelial Growth Factor/Vascular Permeability Factor Enhances Vascular Permeability Via Nitric Oxide and Prostacyclin", Circulation Journal of the American Heart Association, 1998;97; pp. 99-107.
Connolly, D., et. al., "Tumor Vascular Permeability Factor Stimulates Endothelial Cell Growth and Angiogenesis", J. Clin. Invest., Nov. 1989, pp. 1470-1478.

(Continued)

*Primary Examiner*—Jon Weber
*Assistant Examiner*—Abdel A Mohamed
(74) *Attorney, Agent, or Firm*—Schwegman, Lundberg & Woessner, P.A.

(57) ABSTRACT

The present invention provides a method of regulating vascular permeability. A peptide inhibitor of p21-activated kinase has been found to inhibit the increase in vascular permeability induced by several factors. The present invention further provides methods of identifying regulators of vascular permeability. This peptide or other p21-activated kinase inhibitors should therefore be useful to treat disorders where vascular leak is a contributing factor.

19 Claims, 16 Drawing Sheets

OTHER PUBLICATIONS

Eliceiri, Brian P., et. al., "Selective Requirement for Src Kinases during VEGF-Induced Angiogenesis and Vascular Permeability", Molecular Cell., vol. 4, Dec. 1998, pp. 915-924.

Streit, M., et. al., "Thrombospondin-1 Suppresses Wound Healing and Granulation Tissue Formation in the Skin of Transgenic Mice", The EMBO Journal, vol. 19, pp. 3272-3282, 2000.

Mundel, T., et. al., "Type IV Collagen-Derived Angiogenesis Inhibitors", Science Direct, Microvascular Research, 2007, vol. 74, pp. 85-89.

Brinkmann, V., et. al., Pulmonary and Vascular Pharmacology of Sphingosine 1-Phosphate, Current Opinion in Pharmacology, 2006, vol. 6, pp. 244-250.

Skoura, A., et. al., "Essential Role of Sphingosine 1-Phosphate Receptor 2 in Pathological Angiogenesis of the Mouse Retina", The Journal of Clinical Investigation, vol. 117, No. 9, pp. 2506-2516, Sep. 2007.

M. Oo, et. al., "Immunosuppressive and Anti-Angiogenic Sphingosine 1-Phosphate Receptor-1 Agonists Induce Ubiquitinylation and Proteasomal Degradation of the Receptor", Journal of Biological Chemistry, vol. 282, No. 12, pp. 9082-9089, Mar. 23, 2007.

* cited by examiner

*200x*

*400x*

METHOD OF INHIBITING VASCULAR PERMEABILITY

CROSS REFERENCE TO RELATED APPLICATIONS

This application is entitled to priority pursuant to 35 U.S.C. § 119(e) to U.S. provisional patent application No. 60/543,337, filed on Feb. 10, 2004.

US GOVERNMENT RIGHTS

This invention was made with United States Government support under Grant Nos. RO1 GM47214, 1U54 GM64346 and T32 HL07284, awarded by the National Institutes of Health. The United States Government has certain rights in the invention.

BACKGROUND OF THE INVENTION

Passage of fluid and cells out of blood vessels is a significant contributing factor to inflammation, tissue injury, and death in a variety of circumstances. These include ischemic injury, toxic shock, allergic and immune reactions. Vascular permeability is regulated in part by cell-cell adhesions between endothelial cells.

The endothelial cell monolayer lining the vasculature forms a barrier that maintains the integrity of the blood fluid compartment, but permits passage of soluble factors and leukocytes in a regulated manner. Dysregulation of this process produces vascular leakage into underlying tissues, which accompanies the inflammation associated with pathological conditions involving edema (reviewed in Refs. 1-3). Edema associated with vascular permeability also occurs in ischemic injury due to the secretion of vascular endothelial growth factor (VEGF) by hypoxic tissues, which increases tissue damage in animal models of stroke and myocardial infarction (4, 5). Vascular permeability is characterized by altered cell-cell contacts and the appearance of paracellular pores between adjacent cells. Integrity of the endothelial barrier is regulated in part by opposing roles of the actin cytoskeleton in which cortical F-actin stabilizes cell-cell contacts, whereas intracellular stress fibers exert tension to induce permeability (reviewed in Refs. 6 and 7).

Vascular permeability is a precisely regulated function that can contribute positively to immune responses and wound healing; however, leakage of fluid and immune cells into tissues can have serious and life-threatening consequences in a variety of diseases. Fluid accumulation in the lungs because of increased permeability of the pulmonary vasculature leading to respiratory insufficiency is a key element in acute respiratory distress syndrome (51). Vascular leak after stroke or myocardial infarction due to the release of VEGF by hypoxic tissues substantially increases tissue injury after these events (4, 5). Vascular leak and tissue edema contribute to organ failure in sepsis (52).

The small GTPase Rac regulates formation and function of cell-cell adhesions in a number of systems. In epithelial and endothelial cell types, Rac is important for both the assembly of adherens and tight junctions and for their disruption during cell scattering or in response to agonists that trigger permeability (8-12). These complex effects suggest that different Rac effector pathways may differentially regulate cell-cell junctions. Precise temporal and spatial regulation of Rac and its effector pathways are likely to be critical for determining the balance between strengthening and disrupting cell-cell adhesions. However, the downstream pathways that govern these effects are poorly understood.

The p21-activated kinases (PAKs) are serine/threonine kinases activated downstream of Rac and Cdc42 that participate in multiple cellular functions, including motility, morphogenesis, and angiogenesis (13). GTP-bound Rac and Cdc42 bind to inactive PAK, releasing steric constraints imposed by a PAK autoinhibitory domain and permitting PAK auto-phosphorylation and activation. Numerous auto-phosphorylation sites have been identified that serve as markers for activated PAK (14-16). Prominent PAK downstream targets include LIM kinase, which regulates actin polymerization through its effect on cofilin (17), and myosin light chain (MLC). PAK2 catalyzes monophosphorylation of MLC at $Ser^{19}$ to increase contractility and trigger cell retraction (18-20). However, PAK can also inhibit MLC kinase and thereby limit MLC phosphorylation and retraction (21, 22). Serine 141 on PAK2 is a site within the AID sequence that is phosphorylated during activation of the kinase. Phosphorylation of this site contributes to activation by blocking interaction of the AID with the kinase domain to relieve autoinhibition. In endothelial cells, expression of catalytically active PAK1 increased MLC phosphorylation and cell contractility, whereas inhibiting PAK reduced cell contractility (23). Thus, in these cells, the dominant effect of PAK appears to be the promotion of contractility.

There is a long felt need in the art for a method to regulate vascular permeability. The present invention satisfies these needs.

SUMMARY OF THE INVENTION

The present study identifies p21-activated kinase as a key mediator of vascular permeability in vitro and in vivo in response to a wide variety of mediators. PAK may therefore be a promising pharmacological target for treatment of these diseases.

The present invention is directed to compositions and methods for regulating vascular permeability in patients in need thereof, particularly inhibiting vascular permeability. More particularly, the present invention is directed to a method of regulating protein kinase PAK activity and function and vascular permeability. Treatment of patients with a composition comprising a regulator of PAK function or activity may be used to treat patients where vascular leak contributes to, or is caused by, tissue injury, inflammation, shock, disease, or other conditions or disorders associated with aberrant vascular permeability.

Various aspects and embodiments of the invention are described in further detail below.

BRIEF DESCRIPTION OF THE DRAWINGS

FIG. 1. Phosphorylation and localization of PAK in endothelial cells.

FIG. 4. PAK controls permeability.

FIG. 5. Effects of PAK on remodeling of cell-cell junctions and the actin cytoskeleton.

FIG. 6. Regulation of myosin light chain (MLC) phosphorylation by PAK.

DETAILED DESCRIPTION OF THE INVENTION

General Description

Figure 1A:
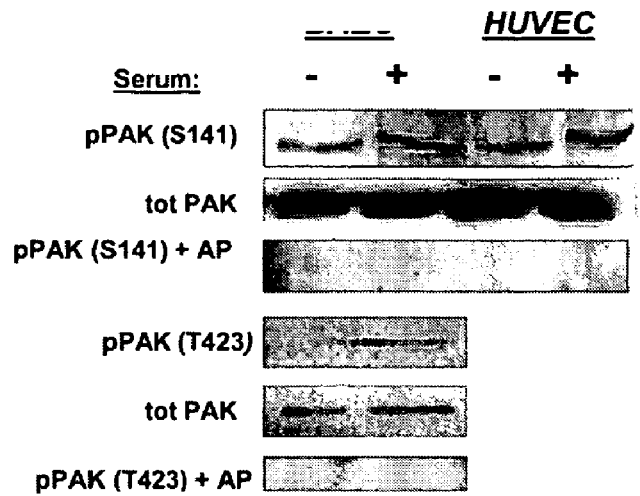
FIG. 1A: confluent endothelial cells were starved for 18 hours in medium with 0.5% serum and then left untreated or treated with 10% serum for 2 hours. The cells were harvested and PAK phosphorylation analyzed by Western blotting. Upper panels, anti-phospho-PAK Ser141 (pPAK (S141)); anti-total PAK1/2/3 (tot PAK); anti-phospho-PAK Ser141 plus antigenic phosphopeptide (pPAK S141+AP) as a competitive inhibitor. Lower panels, BAEC were probed with anti-phospho-PAK Thr423 antibody (pPAK (T423)), anti-total PAK (tot PAK), and pPAK T423 antibody plus antigenic peptide (pPAK T423+AP). Similar results were obtained in three experiments.

The disclosure provided herein tested the role of PAK in the regulation of junctional permeability. It is described herein that either expression of activated PAK, or activation of endogenous PAK, is sufficient to increase permeability across endothelial monolayers. Conversely, blocking PAK function with a peptide which displaces active PAK from cell-cell contacts or expression of the AID to inhibit PAK kinase activity, prevents increases of vascular permeability stimulated by VEGF, bFGF, histamine, TNF, and thrombin. Without wishing to be bound by any particular theory, the very similar responses in HUVECs and BAECs, which represent endothelial cells from different species and different vessels, suggests that the role of PAK in regulating junctional integrity is likely to be highly conserved throughout the vasculature.

The data of the present disclosure suggest that modulation of the effector pathways downstream of Rac is likely to be critical for the decision to scatter versus remaining as a well organized epithelial or endothelial tissue. IQGAP is implicated in stabilizing adherens junctions downstream of Rac and Cdc42 (47). Furthermore, previous studies have shown that Rac activated downstream of specific nucleotide exchange factors preferentially stimulates different effector pathways (48-50).

Abbreviations
  AID—autoinhibitory domain
  BAEC—bovine aortic endothelial cells
  bFGF—basic fibroblast growth factor
  FN—fibronectin
  HRP—horseradish peroxidase
  ip—intraperitoneal
  HUVEC—human umbilical vein endothelial cells
  MLC—myosin light chain
  PAK—p21-activated kinase
  PBS—phosphate-buffered saline
  TNF—tumor necrosis factor
  VEGF—vascular endothelial growth factor Definitions In describing and claiming the invention, the following terminology will be used in accordance with the definitions set forth below.

As used herein, the articles "a" and "an" refer to one or to more than one, i.e., to at least one, of the grammatical object of the article. By way of example, "an element" means one element or more than one element.

As used herein, "amino acids" are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

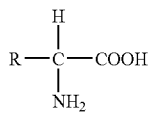

Amino acids may be classified into seven groups on the basis of the side chain R: (1) aliphatic side chains; (2) side chains containing a hydroxylic (OH) group; (3) side chains containing sulfur atoms; (4) side chains containing an acidic or amide group; (5) side chains containing a basic group; (6) side chains containing an aromatic ring; and (7) proline, an imino acid in which the side chain is fused to the amino group.

As used herein, the term "conservative amino acid substitution" is defined herein as exchanges within one of the following five groups:

```
I.    Small aliphatic, nonpolar or slightly polar
      residues:
      Ala, Ser, Thr, Pro, Gly;

II.   Polar, negatively charged residues and their
      amides:
      Asp, Asn, Glu, Gln;

III.  Polar, positively charged residues:
      His, Arg, Lys;

IV.   Large, aliphatic, nonpolar residues:
      Met Leu, Ile, Val, Cys

V.    Large, aromatic residues:
      Phe, Tyr, Trp
```

The nomenclature used to describe the peptide compounds of the present invention follows the conventional practice wherein the amino group is presented to the left and the carboxy group to the right of each amino acid residue. In the formulae representing selected specific embodiments of the present invention, the amino-and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

A "pathoindicative" cell is a cell which, when present in a tissue, is an indication that the animal in which the tissue is located (or from which the tissue was obtained) is afflicted with a disease or disorder.

A "pathogenic" cell is a cell which, when present in a tissue, causes or contributes to a disease or disorder in the animal in which the tissue is located (or from which the tissue was obtained).

A tissue "normally comprises" a cell if one or more of the cell are present in the tissue in an animal not afflicted with a disease or disorder.

A disease, condition, or disorder is "alleviated" if the severity of a symptom of the disease or disorder, the frequency with which such a symptom is experienced by a patient, or both, are reduced.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, a "functional" biological molecule is a biological molecule in a form in which it exhibits a property or activity by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, an "instructional material" includes a publication, a recording, a diagram, or any other medium of expression which can be used to communicate the usefulness of a compound of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, a "ligand" is a compound that specifically binds to a target compound or molecule. A ligand "specifically binds to" or "is specifically reactive with" a compound when the ligand functions in a binding reaction which is determinative of the presence of the compound in a sample of heterogeneous compounds.

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention.

The term "PAK function," as used herein, refers to any activity or function of p21-activated kinase, including, but not limited to, PAK binding with other molecules, kinase activity, autophosphorylation, translocation, activation by other molecules, etc. "PAK function" is used interchangeably with "PAK activity" herein. As used herein, "inhibition of PAK" refers to inhibiting any PAK activity or function, including inhibiting PAK synthesis.

The term "peptide" typically refers to short polypeptides.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

A "recombinant polypeptide" is one which is produced upon expression of a recombinant polynucleotide.

A peptide encompasses a sequence of 2 or more amino acids wherein the amino acids are naturally occurring or synthetic (non-naturally occurring) amino acids. Peptide mimetics include peptides having one or more of the following modifications:

1. peptides wherein one or more of the peptidyl —C(O)NR— linkages (bonds) have been replaced by a non-peptidyl linkage such as a —CH2-carbamate linkage (—CH2OC(O)NR—), a phosphonate linkage, a —CH2-sulfonamide (—CH2-S(O)2NR—) linkage, a urea (—NHC(O)NH—) linkage, a —CH2-secondary amine linkage, or with an alkylated peptidyl linkage (—C(O)NR—) wherein R is C1-C4 alkyl;

2. peptides wherein the N-terminus is derivatized to a —NRR1 group, to a —NRC(O)R group, to a —NRC(O)OR group, to a —NRS(O)2R group, to a —NHC(O)NHR group where R and R1 are hydrogen or C1-C4 alkyl with the proviso that R and R1 are not both hydrogen;

3. peptides wherein the C terminus is derivatized to —C(O)R2 where R2 is selected from the group consisting of C1-C4 alkoxy, and —NR3R4 where R3 and R4 are independently selected from the group consisting of hydrogen and C1-C4 alkyl.

The term "permeability," as used herein, refers to transit of fluid, cell, or debris between or through cells and tissues.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tertbutoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure.

By the term "specifically binds," as used herein, is meant an antibody which recognizes and binds a specific protein, but does not substantially recognize or bind other molecules in a sample, or it means binding between two or more proteins as in part of a cellular regulatory process, where said proteins do not substantially recognize or bind other proteins in a sample.

A "subject" of diagnosis or treatment is a mammal, including a human.

As used herein, the term "treating" includes prophylaxis of the specific disease, disorder, or condition, or alleviation of the symptoms associated with a specific disease, disorder or condition and/or preventing or eliminating said symptoms. A "prophylactic" treatment is a treatment administered to a subject who does not exhibit signs of a disease or exhibits only early signs of the disease for the purpose of decreasing the risk of developing pathology associated with the disease.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The phrase "vascular leak associated disease or disorder" and the like, as used herein, refers to a disease, disorder, injury, or pathological condition which results in vascular leak or which is associated with vascular leak. Thus, the phrase refers to any condition where vascular-leak occurs. Vascular leak, or changes in vascular permeability, occurs in many diseases, disorders, injuries and pathological conditions. For example, such pathological conditions or stimuli include, but are not limited to, tissue damage, ischemia, inflammation, stroke, wound healing, acute respiratory distress syndrome, hypertension, myocardial infarction, sepsis, hypoxia, infection, allergic reactions, thermal injury, x-irradiation, and ultraviolet irradiation. In addition, vascular leak is associated with local tissue inflammation in many diseases. The term "vascular leak associated disease or disorder" is used interchangeably herein with "vascular permeability associated disease or disorder"

EMBODIMENTS OF THE INVENTION

The present invention is based, at least in part, on the discovery that activation and translocation of the protein kinase PAK (p21-activated kinase), an effector for the small GTPases Rac and Cdc42, regulates endothelial cell-cell adhesions, contractility, and leakage across the endothelial cell monolayer in culture. The present invention also demonstrates that regulators of PAK inhibit tissue damage induced by inflammatory agents in vivo.

One embodiment the present invention provides methods for treating and diagnosing states characterized by excessive permeability of the vascular endothelial cell layers. For example, treatment of patients with a PAK regulator may be used where vascular leak contributes to conditions, such as tissue injury, ischemia, inflammation, or shock, or is a result of such conditions. Insofar as PAK expression can be used as an indicator of a condition, such as inflammation, screening tests for monitoring PAK activity, function, or levels are useful in assessing the disease state of an individual.

In one embodiment the invention provides a regulator of vascular permeability which regulates vascular permeability by regulating PAK activity, function, or levels. In one aspect of the invention, the regulator of PAK stimulates PAK activity, function, or levels. In another aspect, the regulator of PAK inhibits PAK activity, function, or levels.

In accordance with one embodiment, a composition is provided comprising a PAK inhibitor and a pharmaceutically acceptable carrier. In one embodiment the composition is formulated for intravenous delivery. The PAK inhibitor may be, for example, an agent which binds to, or blocks, either or both of the kinase domain of PAK and the p21 (e.g., Cdc42 or Rac 1) binding domain of PAK, or the autophosphorylation sites of PAK. In one embodiment, the PAK inhibitor is a short peptide that contains the sequence from PAK that exerts dominant negative activity (Kiosses et al, 2002, Circ. Res. 90:697). This peptide (YGRKKRRQRRRGKPPAPPMRNTSTM; SEQ ID NO:1) consists of the sequence KPPAPPMRNTSTM (SEQ ID NO:2) from the first proline-rich domain of PAK, fused to the polybasic sequence YGRKKRRQRRRG (SEQ ID NO:3) from the HIV TAT protein (Schwarze et al, 1999, Science 285:1569) which promotes entry into cells. The peptide (SEQ ID NO:1) inhibits PAK function similarly to full length dominant negative constructs. The peptide does not block PAK kinase activity per se, but instead displaces PAK from sites of action including cell-cell junctions, which is sufficient to prevent its effects on cellular contractility, migration, and permeability.

In another embodiment, the PAK inhibitor comprises the autoinhibitory domain of PAK, which blocks PAK kinase activity.

The present disclosure also encompasses other PAK regulators for use in the present invention. Assays useful for identifying additional PAK regulators have been described herein as well as in U.S. Pat. No. 6,248,549 and in U.S. patent Publication 20040138133, published Jul. 15, 2004, the disclosures of which are incorporated herein in their entirety.

In another embodiment, the regulator of PAK activity or function can block other proteins or molecules from binding with PAK. In one aspect, the regulator binds with the other proteins or molecules and inhibits them from interacting with PAK. In another aspect, the regulator binds to PAK and inhibits other proteins or molecules from binding with PAK.

In one embodiment, the present invention is directed to a method of inhibiting PAK activity or function. The method comprises the steps of contacting PAK in vitro or in vivo with a PAK inhibitory composition. For example the PAK inhibitory composition may comprise an inhibitory peptide with the sequence YGRKKRRQRRRGKPPAPPMRNTSTM (SEQ ID NO:1), or a peptide identical to YGRKKRRQRRRGKPPAPPMRNTSTM (SEQ ID NO:1) but containing 1, 2 or 3 conservative amino acid substitutions (see Stockton et al., J. Biol. Chem., 2004, 279:45:46621-46630). The above-mentioned inhibitory peptide has been found to block increases in vascular permeability using cultured endothelial cells. This result has been confirmed by expressing another PAK inhibitory sequence, the autoinhibitory domain, which blocks PAK kinase activity. In yet another aspect, the peptide comprises an amino acid sequence selected from the group consisting of SEQ ID NO:1 and SEQ ID NO:2, or biologically active analogs, fragments, homologs, and derivatives thereof. The invention also provides isolated nucleic acids comprising sequences encoding peptides and proteins of the invention.

In one embodiment, a PAK regulator of the present invention inhibits increased vascular permeability in a tissue induced by an inflammatory agent in vivo. In one aspect, the tissue is lung tissue.

In one embodiment, a method of treating a patient suffering from a condition or disease that is associated with excessive vascular permeability is provided. The method comprises the step of administering a composition comprising an effective amount of at least one PAK regulator and a pharmaceutically acceptable carrier. In one aspect, the regulator is an inhibitor of PAK activity or levels. In another aspect, at least one PAK regulator identified by the methods of the invention and a known PAK regulator can be administered to a subject in need thereof. In yet another aspect of the invention, at least one PAK regulator and another drug or medication can be administered to a subject in need thereof.

In on aspect, the PAK regulator acts by regulating PAK transcription. In another aspect, the PAK regulator acts by regulating PAK translation. In yet another aspect, the regulator acts by regulating PAK kinase activity. In a further aspect, the PAK regulator acts by regulating PAK translocation. In yet a further aspect, the PAK regulator acts by inhibiting binding between PAK and other molecules. In one aspect, the PAK regulator is a protein or peptide. In another aspect, the PAK regulator is an antibody.

Antibodies directed against proteins, polypeptides, or peptide fragments thereof of the invention may be generated using methods that are well known in the art. For instance, U.S. patent application Ser. No. 07/481,491, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For the preparation of monoclonal antibodies, any technique which provides for the production of antibody molecules by continuous cell lines in culture may be utilized. For example, the hybridoma technique originally developed by Kohler and Milstein (1975, *Nature* 256:495-497), the trioma technique, the human B-cell hybridoma technique (Kozbor et al., 1983, *Immunology Today* 4:72), and the EBV-hybridoma technique (Cole et al., 1985, in *Monoclonal Antibodies and Cancer Therapy*, Alan R. Liss, Inc., pp. 77-96) may be employed to produce human monoclonal antibodies. In another embodiment, monoclonal antibodies are produced in germ-free animals utilizing the technology described in international application no. PCT/US90/02545, which is incorporated by reference herein in its entirety.

In accordance with the invention, human antibodies may be used and obtained by utilizing human hybridomas (Cote et al., 1983, *Proc. Natl. Acad. Sci. U.S.A.* 80:2026-2030) or by transforming human B cells with EBV virus in vitro (Cole et al., 1985, in *Monoclonal Antibodies and Cancer Therapy*, Alan R. Liss, Inc., pp. 77-96). Furthermore, techniques developed for the production of "chimeric antibodies" (Morrison et al., 1984, *Proc. Natl. Acad. Sci. U.S.A.* 81:6851-6855; Neuberger et al., 1984, *Nature* 312:604-608; Takeda et al., 1985, *Nature* 314:452-454) by splicing the genes from a mouse antibody molecule specific for epitopes of SLLP polypeptides together with genes from a human antibody molecule of appropriate biological activity can be employed; such antibodies are within the scope of the present invention. Once specific monoclonal antibodies have been developed, the preparation of mutants and variants thereof by conventional techniques is also available.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, *Science* 246:1275-1281) are utilized to allow rapid and easy identification of monoclonal Fab fragments possessing the desired specificity for specific antigens, proteins, derivatives, or analogs of the invention.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard. procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein. Further, the antibody of the invention may be "humanized" using the technology described in Wright et al., (supra) and in the references cited therein, and in Gu et al. (1997, Thrombosis and Hematocyst 77(4):755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art.

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/ phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222: 581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol.248:97-105).

In the production of antibodies, screening for the desired antibody can be accomplished by techniques known in the art, e.g., ELISA (enzyme-linked immunosorbent assay). Antibodies generated in accordance with the present invention may include, but are not limited to, polyclonal, monoclonal, chimeric (i.e., "humanized"), and single chain (recombinant) antibodies, Fab fragments, and fragments produced by a Fab expression library.

The peptides of the present invention may be readily prepared by standard, well-established techniques, such as solid-phase peptide synthesis (SPPS) as described by Stewart et al. in Solid Phase Peptide Synthesis, 2nd Edition, 1984, Pierce Chemical Company, Rockford, Ill.; and as described by Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenyl esters. Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well known by those of skill in the art.

Incorporation of N— and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl-blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high-resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide. Prior to its use, the peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as C4-, C8- or C18-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

It will be appreciated, of course, that the peptides or antibodies, derivatives, or fragments thereof may incorporate amino acid residues which are modified without affecting activity. For example, the termini may be derivatized to include blocking groups, i.e. chemical substituents suitable to protect and/or stabilize the N— and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without affect on peptide activity.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present invention are also contemplated, for example, inverted peptides in which all amino acids are substituted with D-amino acid forms.

Acid addition salts of the present invention are also contemplated as functional equivalents. Thus, a peptide in accordance with the present invention treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the invention.

The present invention also provides for homologs of proteins and peptides. Homologs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. To that end, 10 or more conservative amino acid changes typically have no effect on peptide function.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides or antibody fragments which have been modified using ordinary molecular biological techniques so as to improve their resistance to proteolytic degradation or to optimize solubility properties or to render them more suitable as a therapeutic agent. Homologs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

The present invention also provides nucleic acids encoding peptides, proteins, and antibodies of the invention. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

It is not intended that the present invention be limited by the nature of the nucleic acid employed. The target nucleic acid may be native or synthesized nucleic acid. The nucleic acid may be from a viral, bacterial, animal or plant source. The nucleic acid may be DNA or RNA and may exist in a double-stranded, single-stranded or partially double-stranded form. Furthermore, the nucleic acid may be found as part of a virus or other macromolecule. See, e.g., Fasbender et al., 1996, J. Biol. Chem. 272:6479-89 (polylysine condensation of DNA in the form of adenovirus).

Nucleic acids useful in the present invention include, by way of example and not limitation, oligonucleotides and polynucleotides such as antisense DNAs and/or RNAs; ribozymes; DNA for gene therapy; viral fragments including viral DNA and/or RNA; DNA and/or RNA chimeras; mRNA; plasmids; cosmids; genomic DNA; cDNA; gene fragments; various structural forms of DNA including single-stranded DNA, double-stranded DNA, supercoiled DNA and/or triple-helical DNA; Z-DNA; and the like. The nucleic acids may be prepared by any conventional means typically used to prepare nucleic acids in large quantity. For example, DNAs and RNAs may be chemically synthesized using commercially available reagents and synthesizers by methods that are well-known in the art (see, e.g., Gait, 1985, OLIGONUCLEOTIDE SYNTHESIS: A PRACTICAL APPROACH (IRL Press, Oxford, England)). RNAs may be produce in high yield via in vitro transcription using plasmids such as SP65 (Promega Corporation, Madison, Wis.).

In some circumstances, as where increased nuclease stability is desired, nucleic acids having modified internucleoside linkages may be preferred. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide (—CH2-S—CH2), diinethylene-sulfoxide (—CH2-SO—CH2), dimethylene-sulfone (—CH2-SO2-CH2), 2'-O-alkyl, and 2'-deoxy2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein).

The nucleic acids may be purified by any suitable means, as are well known in the art. For example, the nucleic: acids can be purified by reverse phase or ion exchange HPLC, size exclusion chromatography or gel electrophoresis. Of course, the skilled artisan will recognize that the method of purification will depend in part on the size of the DNA to be purified.

The term nucleic acid also specifically includes nucleic acids composed of bases other than the five biologically occurring bases (adenine, guanine, thymine, cytosine and uracil).

The present invention is also directed to pharmaceutical compositions comprising the vascular permeability regulatory compounds of the present invention. More particularly, such compounds can be formulated as pharmaceutical compositions using standard pharmaceutically acceptable carriers, fillers, solublizing agents and stabilizers known to those skilled in the art.

The invention is also directed to methods of administering the compounds of the invention to a subject. In one embodiment, the invention provides a method of treating a subject with a vascular-leak associated disease, disorder, or condition by administering compounds identified using the methods of the invention description. It is preferred that a compound inhibits vascular by at least 10% relative to a control where a compound is not being used to inhibit vascular leak. It is more preferred that a compound of the invention inhibits vascular-leak by at least 25% relative to untreated controls. It is further preferred that a compound of the invention inhibits vascular-leak by at least 50% relative to untreated controls. It is even further preferred that a compound of the invention inhibits vascular-leak by at least 75% relative to untreated controls. It is also preferred that a compound of the invention inhibits vascular-leak by at least 90% relative to untreated controls. In yet another aspect, it is preferred that a compound of the invention inhibits vascular-leak by at least 95% relative to untreated controls. In one aspect of the invention, vascular-leak is inhibited due to inhibition of PAK function or activity.

Pharmaceutical compositions comprising the present compounds are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

In accordance with one embodiment, a method of treating a vascular permeability associated disease, disorder, or condition in a subject in need such treatment is provided. The method comprises administering a pharmaceutical composition comprising at least one vascular permeability regulatory compound of the present invention to a patient in need thereof. Compounds identified by the methods of the invention which regulate vascular permeability can be administered with known vascular permeability compounds or other medications as well. Preferably the compounds are administered to a human.

The invention also encompasses the use pharmaceutical compositions of an appropriate compound, homolog, fragment, analog, or derivative thereof to practice the methods of the invention, the composition comprising at least one appropriate compound, homolog, fragment, analog, or derivative thereof and a pharmaceutically-acceptable carrier.

The pharmaceutical compositions useful for practicing the invention may be administered to deliver a dose of between 1 ng/kg/day and 100 mg/kg/day. Pharmaceutical compositions that are useful in the methods of the invention may be administered systemically in oral solid formulations, ophthalmic, suppository, aerosol, topical or other similar formulations. In addition to the appropriate compound, such pharmaceutical compositions may contain pharmaceutically-acceptable carriers and other ingredients known to enhance and facilitate drug administration. Other possible formulations, such as nanoparticles, liposomes, resealed erythrocytes, and immunologically based systems may also be used to administer an appropriate compound according to the methods of the invention.

Compounds which are identified using any of the methods described herein may be formulated and administered to a mammal for treatment of the diseases disclosed herein are now described.

The invention encompasses the preparation and use of pharmaceutical compositions comprising a compound useful for treatment of the conditions, disorders, anddiseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys. Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology. A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc. Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin. Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose.

Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl para hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil in water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may also be prepared, packaged, or sold in a formulation suitable for rectal administration, vaginal administration, parenteral administration The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non toxic parenterally acceptable diluent or solvent, such as water or 1,3 butane diol, for example. Other acceptable diluents and solvents include, but are not limited to, Ringer's solution, isotonic sodium chloride solution, and fixed oils such as synthetic mono or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi liquid preparations such as liniments, lotions, oil in water or water in oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self propelling solvent/powder dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein. A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1/1.0% (w/w) solution or suspension of the active ingredient in an aqueous or oily liquid carrier. Such drops may further comprise buffering agents, salts, or one or more other of the additional ingredients described herein. Other opthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference. Typically, dosages of the compound of the invention which may be administered to an animal, preferably a human, range in amount from 1 µg to about 100 g per kilogram of body weight of the subject. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the subject.

The compound may be administered to a subject as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the subject, etc.

The invention also includes a kit comprising a compound of the invention and an instructional material which describes administering the composition to a cell or a tissue of a subject. In another embodiment, this kit comprises a (preferably sterile) solvent suitable for dissolving or suspending the composition of the invention prior to administering the compound to the subject. The invention also provides a kit for identifying a regulator of vascular permeability as described herein, said kit comprising a sample of tissue or cells comprising a p21 -activated kinase, a standard regulator of p21-activated kinase, an applicator, and an instructional material for the use thereof.

Without further description, it is believed that one of ordinary skill in the art can, suing the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXAMPLES

The invention is now described with reference to the following examples. These examples are provided for the purpose of illustration only and the invention should in no way be construed as being limited to these examples, but rather should be construed to encompass any and all variations which become evident as a result of the teachings provided herein.

General Methods:

Tissue Culture—Bovine aortic endothelial cells (BAEC) (a generous gift from Dr. Helene Sage, Hope Heart Institute, Seattle Wash.) were grown in high glucose Dulbecco's modified Eagle's medium supplemented with 10% bovine calf serum (Atlanta Biologicals, Atlanta, Ga.), 100 µg/ml dihydrostreptomycin, and 60 units/ml penicillin (Sigma) in a humidified 37° C. incubator with 5% CO2. Stock cells were passaged 2-3 times/week and used between passages 9-14. Prior to the experiments, the cells were incubated in medium with 0.5% serum for 18 hours. Human umbilical vein endothelial cells (HUVECs) were a gift from Dr. Brett Blackman (University of Virginia Cardiovascular Research Center) and were grown in EGM-2 medium (Clonetics), supplemented with 10% fetal bovine serum (Atlanta Biologicals) and used at passages 3-10 (as described in Stockton et al., 2004, J. Biol. Chem., 279:45:46621-46630)

Reagents—VEGF was from Genentech. Active Rac expression constructs pcDNA3-V12Rac and pEGFP-V12Rac, inactive Rac pcDNA3-N17Rac, and pEGFP-N17Rac were described previously (24, 25). Vectors for wild-type PAK1 (pcDNA3-PAK1), active PAK1 (pCMV6-T423E PAK), and dominant negative PAK1 (pCMV6-H83R/H86R/H299R) were described by Kiosses et al. (23). The PAK autoinhibitory domain (AID), comprising residues 83-149, was cloned into the pDsRed1-N1 vector (Clontech) using KpnI and BamHI sites. The PAK function-blocking peptide (26) comprises PAK1 residues 1-13, which bind the Nck SH3 domain linked to the human immunodeficiency virus Tat polybasic sequence in order to facilitate membrane permeability. The control peptide contains mutations in two prolines that are required for SH3 domain binding. The peptides were synthesized by the Scripps Research Institute protein synthesis facility.

Transfections—Cells were grown to confluence on 22-mm glass coverslips, tissue culture plates, or Transwell filters, all coated with fibronectin (FN) at 10 µg/ml in phosphate-buffered saline (PBS). Plasmid DNA was transfected using Effectene (Invitrogen) in growth medium according to the manufacturer's protocols. The control cells were transfected with pEGFP-C1, pCMV6, or pcDNA3 as vector-only controls. The transfected cells were grown 24 h in Dulbecco's modified Eagle's medium 10% serum and then transferred to starvation medium 18 h before use.

Fluorescence Imaging—Cells were grown to confluence on FN-coated glass coverslips in medium with 10% serum and then serum-starved for 18 h. Treated cells were washed once with PBS, fixed for 20 min in 3.5% formaldehyde, and permeabilized for 10 min with 0.1% Triton X-100 in PBS. Coverslips were blocked for 30 min with 10% goat serum in PBS and then incubated for 12 h at 4° C. with rabbit anti-phospho-PAK Ser141 (BioSource International), goat anti-PAK1/2/3 (BioSource International), mouse anti-catenin (Santa Cruz Biotechnology) at the ratio of 1:500, or rabbit anti-phospho-MLC (BioSource International) at the ratio 1:500. Control coverslips, for comparison with the anti-phospho antibody treatments, were probed with the same antibody dilution mixed 1:1 with the antigenic phosphopeptide. Coverslips were washed with PBS and incubated with species-specific Alexa 488, 568, or Cy5-labeled anti-IgG at 1:1,000 for 2 h at room temperature. Some coverslips were washed again and incubated for 30 min in 0.66 µM Alexa-conjugated phalloidin (Molecular Probes). Coverslips were mounted on glass slides with Immunofluore mounting medium (ICN Immunobiologicals).

For epifluorescence microphotography, images were acquired using a Nikon Diaphot inverted fluorescence microscope with a Roper charge-coupled device camera. For confocal microscopy, images were acquired using either a Bio-Rad Radiance 2100 coupled to a Nikon scope, or an Olympus Fluoview 2-laser confocal microscope. Digitized images were processed using either Innovision ISEE or Adobe PhotoShop software.

Western Blots—Confluent cells were starved in 0.5% serum for 18 h, treated as described in the legends to FIGS. 1, 2, 3 and 6, washed with cold PBS, and then harvested by scraping in cold lysis buffer (25 mM Tris, pH 7.4, 1% Nonidet P-40, 0.5% sodium deoxycholate, 137 mM NaCl, 50 µM EDTA, 10 µg/ml each aprotinin and leupeptin, 1 mM phenylmethylsulfonyl fluoride). Lysates were centrifuged for 10 min at 13,000×g. The supernatants were diluted to equivalent protein concentrations and separated on a 10% SDS-polyacrylamide gel. Protein was transferred to polyvinylidene difluoride membrane, and blots were probed with primary antibodies (described under "Fluorescence Imaging") followed by horseradish peroxidase-conjugated secondary antibodies (Jackson ImmunoResearch, Inc.). Rabbit anti-phospho-PAK Thr423 antibody was from BioSource International. Blots were washed and developed using ECL (Amersham Biosciences).

Monolayer Permeability and Paracellular Pore Formation Assays—Cells were plated onto FN-coated polycarbonate membranes (3.0-µ pore size; Transwell, Costar) at $6 \times 10^4$ cells/$cm^2$ and cultured for 4 days with medium changes every other day until confluence was reached. Where indicated, cells in normal growth medium with 10% serum were transfected 36 hours before the assays. For experiments using a PAK-blocking or control peptide, medium in the upper chamber was replaced with medium containing peptides for 60 minutes before the experiment; control cell chambers received replacement medium containing vehicle only. In experiments using growth factors or other stimulants, medium containing those additions was added to the upper chambers for 30-60 minutes, as indicated. Horseradish peroxidase (HRP, Sigma) was then added to the upper chambers at a final concentration of 1.5 µg/ml. After 20 minutes, the filters were removed and immediately fixed in 3.5% paraformaldehyde for 30 minutes. Medium was harvested from the lower chamber, and HRP activity was determined calorimetrically by absorbance at 490 nm to detect the O-phenylenediamine reaction product after 15 minutes of incubation with 0.5 mM guaiacol, 50 mM $Na_2HPO_4$, and 0.6 mM $H_2O_2$. The mean HRP concentration in the lower chamber medium from cells in variously treated wells was normalized to the HRP concentration in the control wells transfected with vector only or treated with vehicle only, and the results were graphed as means±S.E. of 4 to 7 experiments. To quantify paracellular pore formation and correlate to permeability, the fixed cell monolayer-covered filters were stained for 2 hours with Coomassie Blue (0.25% in 1:1:2 of methanol:glacial acetic acid:double distilled (dd)$H_2O$), destained in the same solution minus dye, rinsed in dd$H_2O$, and air-dried. Stained cell monolayers were examined by phase-contrast microscopy and the number of pores/$mm^2$ of filter surface counted in eight randomly selected fields per filter. These values were normalized to the number of pores in the control cells.

Statistical Analysis—For all quantitative assays, data from four to eight experiments were analyzed for statistical significance by analysis of variance (ANOVA) or Student's t test, as appropriate, using SigmaStat analytical software (Jandel Scientific) and are shown graphically as means±S.E. Photographic or blot images shown are representative of results seen consistently in multiple experiments.

Example 1

PAK Phosphorylation and Translocation to Cell-Cell Junctions

PAK1, -2, and -3 are held in an inactive conformation via an interaction of the kinase domain with a sequence in the regulatory N terminus named the AID (13). Binding of activated Rac or Cdc42 to PAK leads to autophosphorylation of several sites that confer sustained increases in PAK kinase activity (16, 27). One of these sites, $Ser^{141}$ in PAK2 (which corresponds to $Ser^{144}$ in PAK1), is within the AID and its phosphorylation contributes to activation by blocking the interaction of the AID with the kinase domain. To localize activated PAK in endothelial cells, we therefore utilized an antibody that specifically recognizes the phosphorylated Ser$^{141}$ site.

To initially evaluate PAK phosphorylation in endothelial cells in response to serum, confluent bovine aortic and human umbilical vein endothelial cells (BAEC and HUVEC, respectively) were serum-starved (0.5% serum) for 18 hours and then stimulated with 10% serum. Western blotting with anti-phospho-PAK Ser$^{141}$ antibody showed that serum stimulation increased PAK phosphorylation in both cell types (FIG. 1A, upper panels), consistent with previous studies that demonstrated increased PAK kinase activity in endothelial cells treated with serum or growth factors (28). Western blots of BAEC lysates using an antibody specific for PAK phosphorylated at Thr$^{423}$ confirmed the results seen with the phospho-Ser$^{141}$ antibody (FIG. 1A, lower panels).

Figure 1B:
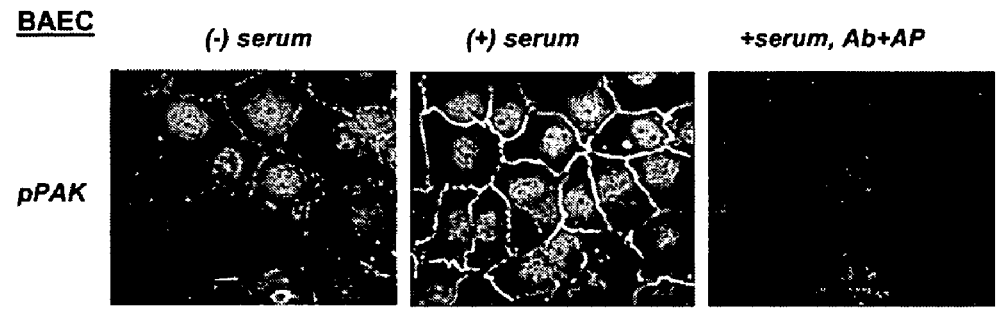
FIG. 1B: cells on FN-coated glass coverslips were treated as described in FIG. 1A, either with (+) or without (−) 10% serum. The cells were fixed and stained with anti-phospho-PAK Ser141 (pPAK) or anti-total PAK1/2/3 (tot PAK) as indicated. As a control, cells were stained with anti-phospho-PAK plus competitive phosphopeptide (+serum, Ab+AP). Scale bar=50μ. Similar results were obtained in three experiments.
Figure 1B:
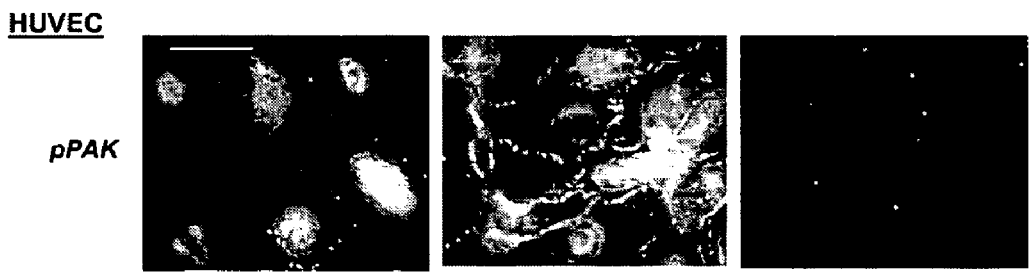

Fluorescence staining of similarly treated cells with anti-phospho-PAK Ser$^{141}$ (pPAK) also showed an increase in PAK phosphorylation in response to serum, with the activated fraction of the protein localized mainly to cell-cell junctions (FIG. 1B). Staining with an antibody that recognizes the total pool of PAK1, -2, and -3 (FIG. 1B, tot PAK) also showed an increase in the staining at cell-cell borders plus a large amount of diffuse cytoplasmic fluorescence that presumably represents the unphosphorylated fraction. The phosphorylated PAK antigenic peptide blocked staining by the phospho-PAK antibody (FIG. 1, +serum, Ab+AP), demonstrating that the pattern is specific. Taken together, these data show that PAK is autophosphorylated on Ser$^{141}$ in response to serum and that the phosphorylated fraction localizes specifically to cell-cell contacts.

Example 2

Rac Regulation of PAK Phosphorylation

Figure 2:
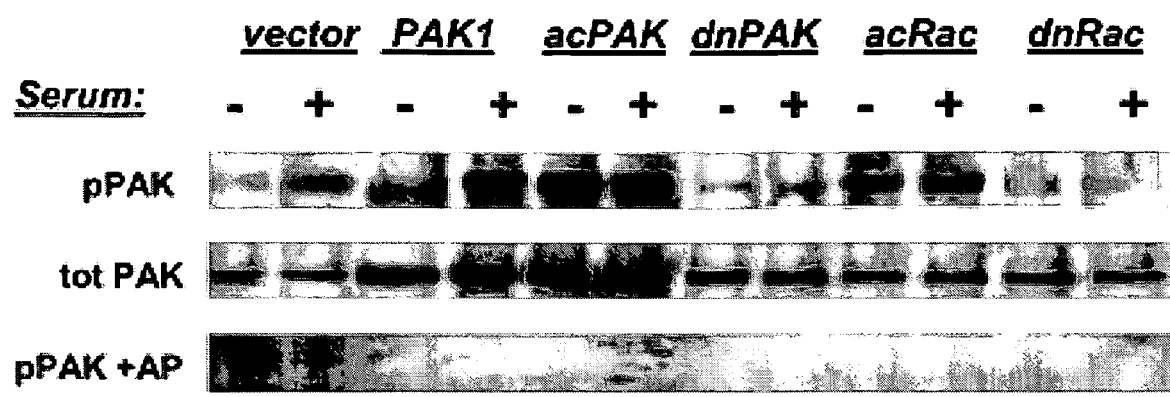
FIG. 2. PAK activation is downstream of Rac. Confluent BAEC were transiently transfected with vector only (vector), wt PAK1 (PAK1), constitutively active T423E PAK (acPAK), dominant negative (H83R/H86R/H299R) PAK (dnPAK), constitutively active Rac (acRac), or dominant negative inactive Rac (dnRac). Cultures were serum-starved (−) or in 10% serum (+); cells were lysed and analyzed by Western blotting. Upper row, anti-phospho-PAK Ser141 (pPAK); middle row, anti-total PAK1/2/3 (tot PAK); and lower row, anti-phospho-PAK plus competitive phospho-peptide (pPAK+AP). Similar results were obtained in four experiments FIG. 3. PAK inhibitory peptide prevents PAK junctional translocation but not phosphorylation.
Figure 3A:
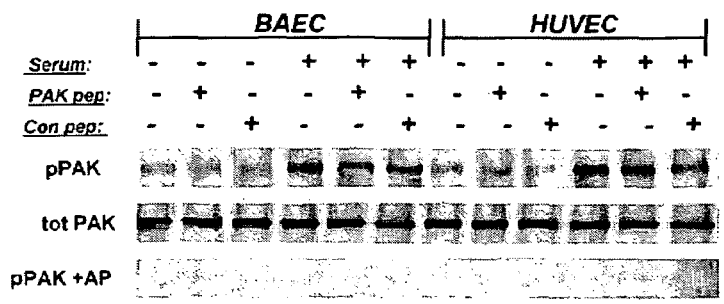
FIG. 3A: confluent endothelial cells were serum-starved (0.5%) for 18 hours and treated without (−) or with (+) 10% serum. All were treated for 60 minutes with 20 μg/ml of PAK-blocking peptide (+PAK pep; SEQ ID NO:1) or control peptide (+con pep) as indicated. The cell lysates were analyzed by Western blotting with anti-phospho-PAK (pPAK), total PAK (tot PAK) or anti-phospho-PAK antibody plus antigenic phosphopeptide (pPAK+AP).
Figure 3B:
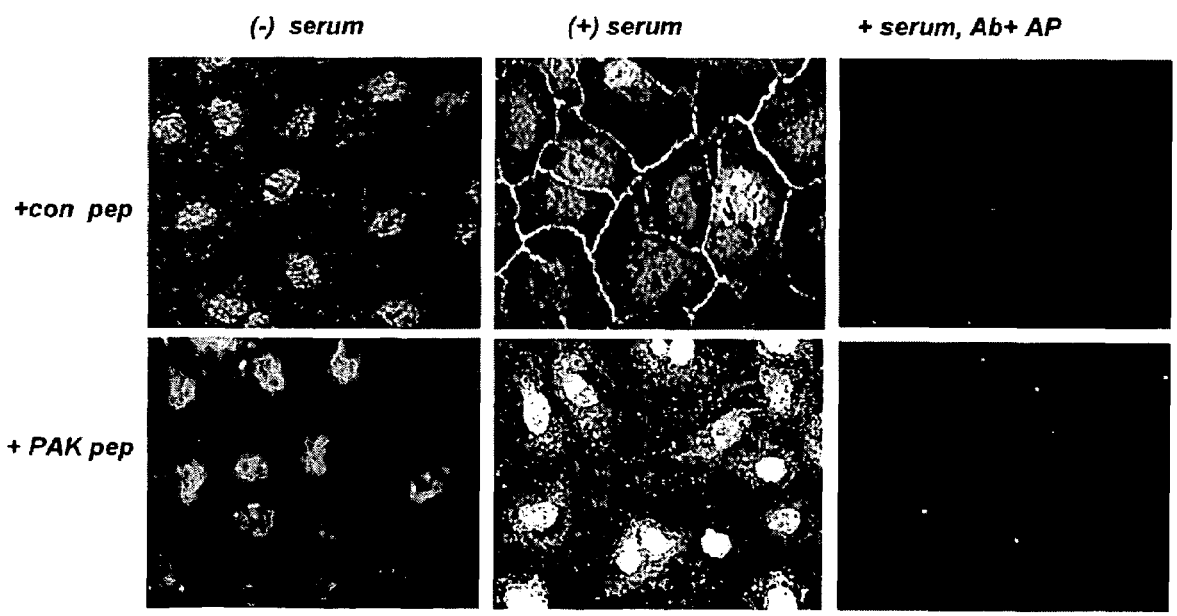
FIG. 3B: cells on coverslips were treated as described in FIG. 3A, fixed, and stained with anti-phospho-PAK Ser141 antibody, alone or with antigenic phosphopeptide (+serum, Ab+AP). Scale bar=50μ.

To confirm these results and evaluate the involvement of Rac upstream of PAK activation, BAEC were transiently transfected to overexpress wild-type PAK1 (FIG. 2, PAK1), constitutively active T423E PAK1 (acPAK), dominant negative (H83R/H86R/H299R) PAK1 (dnPAK), constitutively active V12Rac (acRac), or a dominant negative N17Rac (dnRac). Green fluorescent protein vector was included in all transfections, and transfection efficiency for these experiments was 30-35%, when green fluorescent protein expressors were scored under a low power objective (although this value is probably an underestimate because lower expressors may be missed). Transfected cells were serum-starved for 18 hours and were then treated with 10% serum for 2 hours or were left untreated. Western blots of cell lysates were probed with the phospho-PAK Ser$^{141}$ antibody (pPAK), total PAK antibody (tot PAK), or phospho-PAK antibody in the presence of the antigenic phosphopeptide (pPAK+AP) (FIG. 2). Cells expressing wtPAK1 had increased levels of Ser$^{141}$ phosphorylation, which was further increased after serum stimulation. The active PAK mutant showed higher phosphorylation, which was not further affected by serum. DnPAK transfection reduced levels of phospho-PAK even in the presence of serum. Active Rac also increased PAK phosphorylation both with and without serum, whereas dnRac suppressed PAK phosphorylation. Efficient blocking by the antigenic phosphopeptide demonstrates the specificity of the phospho-PAK antibody. Without wishing to be bound by any particular theory, these results suggest that Rac is the major upstream regulator of PAK activation under these conditions.

Example 3

Effect of a PAK Function-Blocking Peptide

Previous work mapped the inhibitory sequences responsible for the dominant negative effects of kinase-dead PAK in endothelial cells to the first proline-rich repeat that mediates binding to the SH3 domain of Nck (23). A synthetic peptide in which this sequence was fused to the polybasic sequence from the human immunodeficiency virus Tat protein to facilitate cell entry had a very similar effect, reducing endothelial cell motility and contractility (26). The peptide did not appear to inhibit PAK kinase activity but did prevent its translocation to sites of action, which, in those studies with cells at low density, were actin stress fibers. We therefore asked whether this peptide might also limit pPAK translocation to cell-cell borders. BAECs and HUVECs were incubated with either the PAK-blocking peptide or the control peptide in which two critical prolines are mutated to prevent binding to SH3 domains. Western blots of lysates from these cells (FIG. 3A) showed that neither peptide altered PAK phosphorylation with or without serum, consistent with published data (26). Staining of similarly treated BAECs (FIG. 3B) showed that the PAK-blocking peptide (+PAK pep) inhibited phospho-PAK translocation to cell-cell junctions in response to serum. Instead, greater phospho-PAK staining was observed in the cytosol and nucleus. The control peptide (+con pep) had no effect, and similar results were obtained with HUVECs (not shown). The PAK peptide therefore abrogates localization of phospho-PAK to cell-cell contacts in endothelial cells.

Example 4

PAK Regulates Monolayer Permeability

Figure 4A:
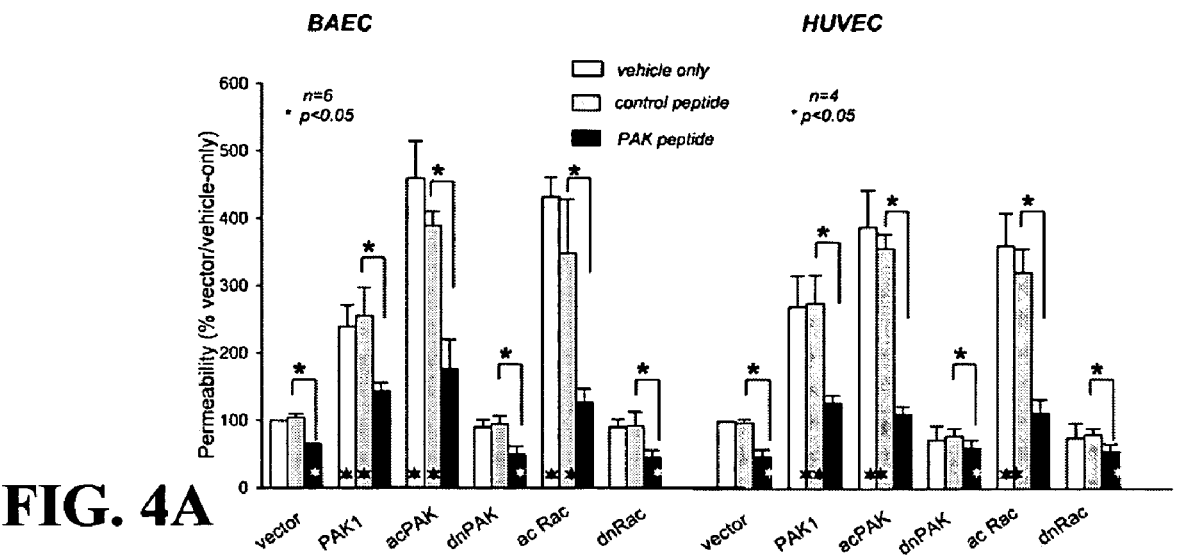
FIG. 4A: BAEC (left graph) and HUVEC (right graph) were grown to confluence on FN-coated 3.0-μ pore Boyden chamber filters in normal growth medium with 10% serum and then transiently transfected with vector only (vector), wt PAK1 (PAK1), active PAK1 (acPAK), dominant negative PAK1 (dnPAK), active Rac (acRac) or dominant negative Rac (dnRac). Cells were incubated in medium with 0.5% serum for 18 hours, and then the upper chamber medium was replaced with medium containing vehicle only (white bars), 20 μg/ml of either control peptide (gray bars) or PAK-blocking peptide (black bars) for 60 minutes. Monolayer permeability was assayed by peroxidase leak assay as described in "Examples". Asterisks within the bars indicate significant difference compared with control vector-only, vehicle-only cells. Asterisks above the bars indicate significant difference compared with vector-only plus control peptide cells of each transfected type.

Junctional localization of phosphorylated and presumably activated PAK suggested a possible role in regulation of permeability across the endothelial monolayer. To test this idea, BAECs and HUVECs grown on filters with 3.0-μm pores were transiently transfected with wtPAK1, active or dnPAK, or active or dnRac. Movement of HRP across the filters was then measured. Overexpression of wtPAK1 increased HRP movement >2-fold in both cell types, whereas both active PAK and active Rac increased movement by greater amounts (FIG. 4A). The PAK-blocking peptide (FIG. 4A, black bars) strongly inhibited this increase in permeability, whereas the control peptide (gray bars) had no statistically significant effects. These data identify a role for PAK in the regulation of junctional permeability in endothelial cells.

Example 5

Growth Factor and Cytokine-Stimulated Permeability

Figure 4B:
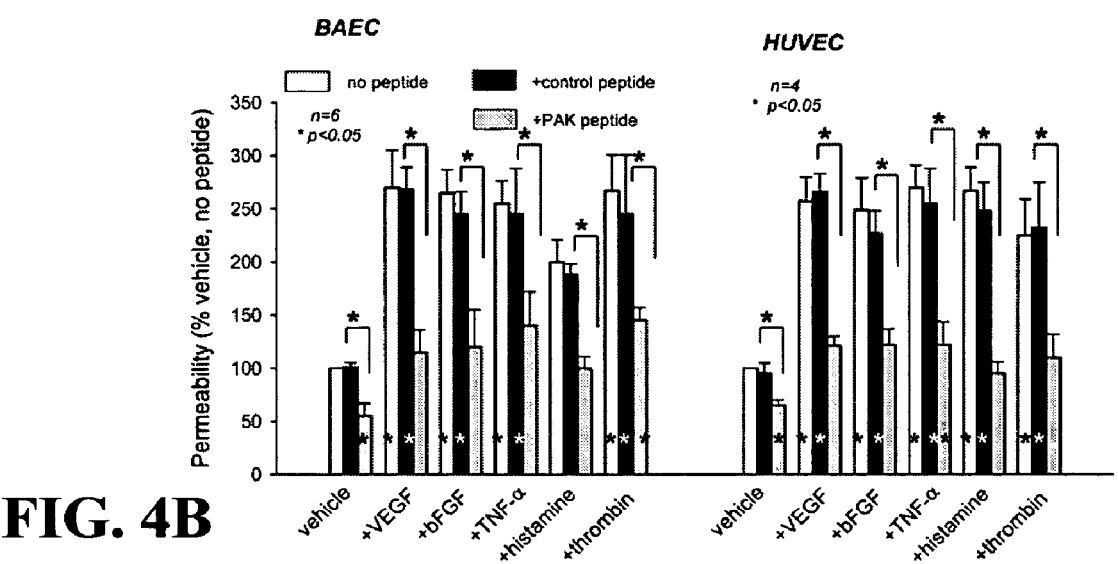
FIG. 4B: BAEC (left graph) or HUVEC (right graph) on FN-coated filters were treated with vehicle only (white bars), control peptide (black bars), or PAK peptide (gray bars) as described in FIG. 4A and then were treated as indicated with 25 ng/ml VEGF (+VEGF), 25 ng/ml bFGF (+bFGF), 10 ng/ml TNFα, 10 μM histamine, or 0.1 units/ml thrombin for 30 minutes.
Figure 4C:
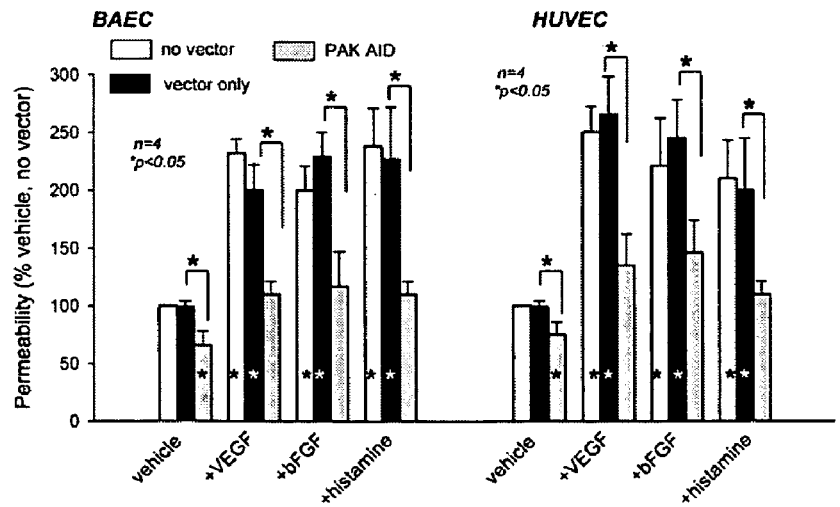
FIG. 4C, cells grown as described in FIG. 4A and 4B were mock-transfected (no vector, white bars) or transiently transfected with vector-only (black bars) or the PAK autoinhibitory domain (PAK AID, gray bars). The cells were treated with vehicle only, VEGF, bFGF, or histamine as described above for 30 minutes and then permeability assayed as described in "Examples".

Vascular permeability is regulated by a variety of soluble cytokines and factors. VEGF is one such factor (4, 5); similarly, bFGF, histamine, thrombin, and TNF also increase vascular permeability. Therefore, the effect of the PAK inhibitory peptide on permeability induced by these agents was examined. The addition of VEGF induced a 2-3-fold increase in movement of HRP across the endothelial monolayer, which was almost completely blocked by the PAK peptide (gray bars) in BAEC and HUVEC (FIG. 4B). The control peptide (black bars) had no detectable effect. These effects correlated with the accumulation of phospho-S$^{141}$ PAK at cell-cell contacts (FIG. 5). To confirm this result, cells were transiently transfected with a construct coding for AID from PAK1 (FIG. 4C). Although control empty vector (black bars) had no significant effect, the AID construct (gray bars) efficiently blocked VEGF-induced permeability. The other cytokines tested had similar effects on permeability, which were also blocked by the inhibitory PAK peptide and the AID (FIG. 4, B and C). These results show that PAK activity is required for induction of vascular leak by VEGF and other factors.

Example 6

Role of Contractility

Figure 5A:
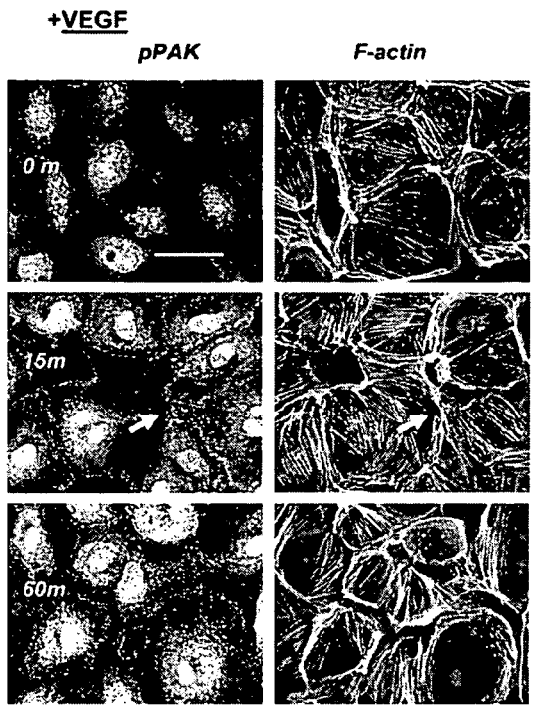
FIG. 5A: confluent BAECs on coverslips were serum-starved for 18 hours and then treated with 25 ng/ml VEGF. The cells were fixed and stained for phospho-PAK and F-actin. Images show phospho-PAK (pPAK) and F-actin (F-actin) at the indicated times after the addition of VEGF. White arrows indicate pores between cells. Scale bar=50μ.
Figure 5B:
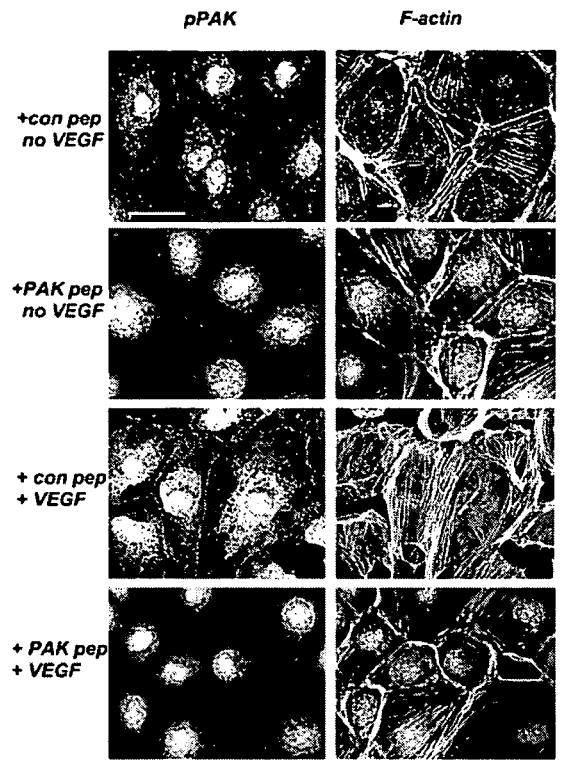
FIG. 5B: phospho-PAK (pPAK) and F-actin (F-actin) are shown in cells prepared and treated as described in FIG. 5A after 60 minutes with VEGF with peptide additions. The cells were treated with 20 μg/ml control peptide (+con pep) or 20 μg/ml PAK-blocking peptide (+PAK pep) with or without 25 ng/ml of VEGF as indicated. Scale bar=50μ.
Figure 5C:
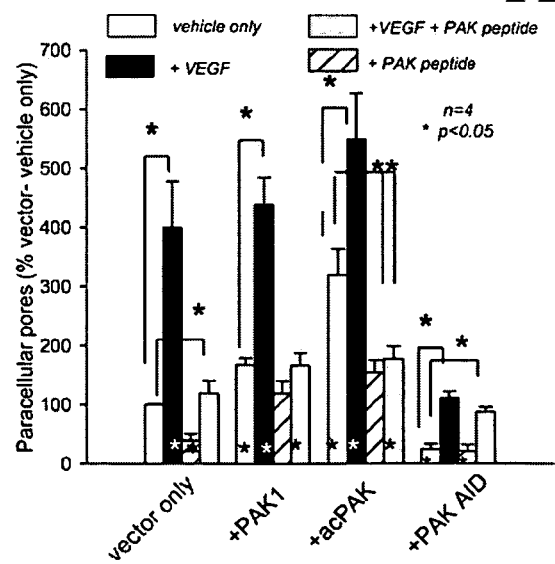
FIG. 5C: cells on filters were transfected with vector only (vector only), wtPAK1 (+PAK1), constitutively active PAK (+acPAK), or the PAK-AID (+PAK AID). Serum-starved cells were treated with vehicle only (white bars), PAK peptide only (striped bars), VEGF only (black bars), or VEGF plus PAK peptide (gray bars), as described in FIG. 5B. Values are the means+S.E. of four experiments normalized to the control treatment for that experiment. Asterisks within the bars indicate significant difference compared with control vector-only, vehicle-only cells. Asterisks above the bars indicate significant difference compared with vehicle-only treatments within each type of transfected cell.

The results with the PAK AID were surprising in that transfection efficiencies were below 50%, and yet the increase in permeability was almost completely inhibited. In considering possible explanations for this result, we recalled that myosin-dependent contractility is well known to regulate cell-cell junctions and permeability across endothelial or epithelial monolayers (29-32). Although both negative or positive effects of PAK on myosin light chain phosphorylation have been reported (18, 19, 33-35), in endothelial cells, PAK clearly promotes myosin phosphorylation and cell contractility (23, 26). Staining of treated cells with rhodamine-phalloidin to visualize F-actin showed first that VEGF addition to BAEC monolayers induced rapid formation of spaces or pores between the cells within 15 minutes, followed at later times by more general separation of adjacent cells (FIG. 5A). Both localization of phospho-PAK to cell-cell contacts and formation of intercellular spaces were largely blocked by PAK peptide but not control peptide (FIG. 5B). When the formation of pores between adjacent cells was examined, BAEC transfected with active PAK induced pores in the absence of VEGF (FIG. 5C), consistent with results from permeability assays, whereas the PAK AID and the PAK peptide inhibited pore formation. These results show alterations in monolayer organization associated with permeability.

Figure 6A:
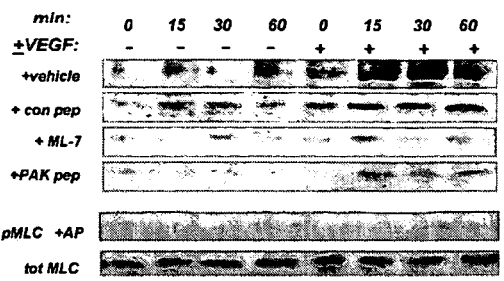
FIG. 6A: confluent BAEC on FN were treated with vehicle only (+vehicle), 20 μg/ml control peptide (+con pep), 20 μg/ml PAK-blocking peptide (+PAK pep; SEQ ID NO:1), 5 μM ML7 (+ML7) with (+) or without (−) 25 ng/ml VEGF. Cells were harvested at the indicated times post-addition of VEGF and analyzed by Western blotting for phosphorylated MLC (upper four rows), total MLC (bottom lower row, tot MLC), or phospho-MLC antibody plus antigenic peptide (top lower strip, pMLC+AP) to demonstrate antibody specificity.
Figure 6B:
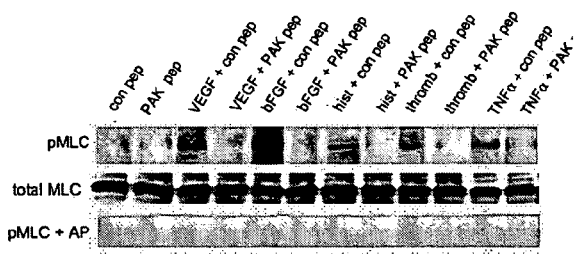
FIG. 6B: as described in A, BAEC were pretreated with 20 μg/ml control peptide (+con pep) or PAK-blocking peptide (+PAK pep) followed by 25 ng/ml of VEGF, 25 ng/ml bFGF, 10 μM histamine, 0.1 units/ml thrombin, or 10 ng/ml of TNF. Upper row, anti-phospho-MLC (pMLC); middle row, total MLC (total MLC); and lower row, pMLC plus an antigenic phospho-peptide (pMLC+AP).
Figure 6D:
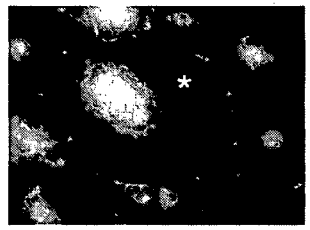
FIG. 6D: BAEC on coverslips were transiently transfected to express the PAK AID and then treated with 25 ng/ml VEGF for 30 min, fixed, and stained for -catenin. Cells expressing the AID construct (asterisk) tended to be extremely enlarged, whereas adjacent nonexpressing cells remained smaller and unable to detach.
Figure 6E:
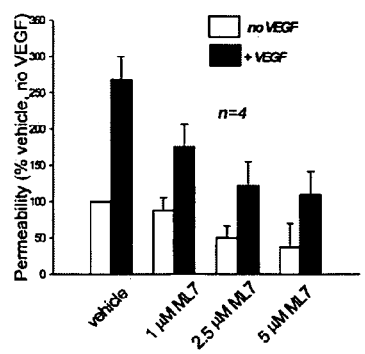
FIG. 6E: confluent BAEC on Transwell 3.0-μm filters were starved in medium with 0.5% serum for 18 h and then treated without (white bars) or with 25 ng/ml VEGF (black bars) and with vehicle only (vehicle) or with 1.0, 2.5, or 5.0 μM ML7 for 60 min. Permeability was assayed as described under "Experimental Procedures."
Figure 6C:
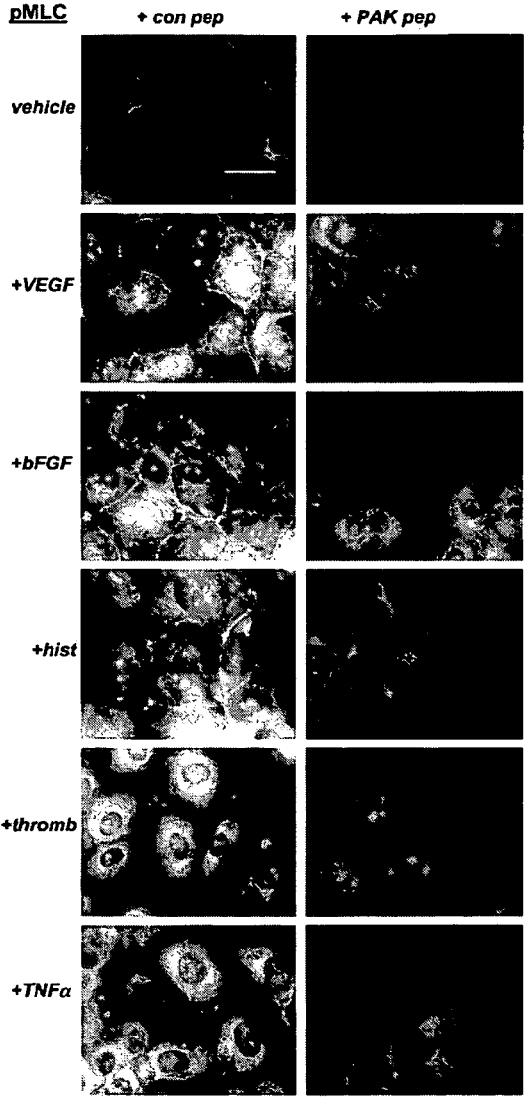
FIG. 6C: BAEC on coverslips were incubated as described in B with control peptide (con pep) or the PAK peptide (PAK pep) followed by 30 min of cytokines as indicated. The cells were then fixed and stained for phospho-MLC.

Visualization of the actin cytoskeleton in BAEC treated with VEGF showed that increased permeability and pore formation correlated with increases in the intensity of staining for actin bundles both at cell-cell borders and spanning the cell (FIG. 5A), as described previously (36-39). Treatment with the PAK-blocking peptide (FIG. 5B) did not dramatically affect the number or intensity of actin stress fibers, but this result is consistent with previous studies that showed a decrease in contractility despite persistence of bundled actin cables (23). Because PAK is known to increase endothelial cell contractility, we assayed myosin phosphorylation in this system. Western blotting with an anti-phospho-MLC antibody showed that MLC phosphorylation induced by VEGF was inhibited by the PAK peptide nearly as well as the MLC kinase inhibitor ML7 (FIG. 6A). PAK peptide also inhibited MLC phosphorylation stimulated by bFGF, histamine, thrombin, and TNF (FIG. 6B). Staining for phospho-MLC in monolayer cells treated with these factors also demonstrated phospho-MLC localization to cell-cell junctions, which was abrogated by the PAK inhibitory peptide (FIG. 6C). We also observed, as has been noted previously (32, 40), that anti-phospho-MLC stained actin stress fibers at the basal surface (data not shown); however, these structures were much less evident at higher focal planes where junctional staining was most prominent (FIG. 6C).

Without wishing to be bound by any particular theory, these results provide a possible explanation for the dominant effect of the PAK AID in transiently transfected cells. Decreases in tension in a fraction of the population may be sufficient to prevent breakup of cell-cell junctions where tension must be exerted from both sides of a junction. When one-half of the junctional pair is relaxed because of a decrease in myosin phosphorylation, it may undergo an increase in cell spreading when its neighbors contract. Indeed, we often noted large, well spread PAK AID-positive cells (FIG. 6D, white asterisk) surrounded by smaller untransfected cells in the culture (FIG. 6D). To test the importance of myosin phosphorylation, cells were treated with the myosin light chain kinase inhibitor ML7. A dose-dependent decrease in both baseline and VEGF-stimulated permeability was observed (FIG. 6E). The highly efficient inhibition by transient transfection with PAK AID is therefore consistent with a myosin-dependent mechanism.

Example 7

Effects on Adherens Junctions

Figure 7:
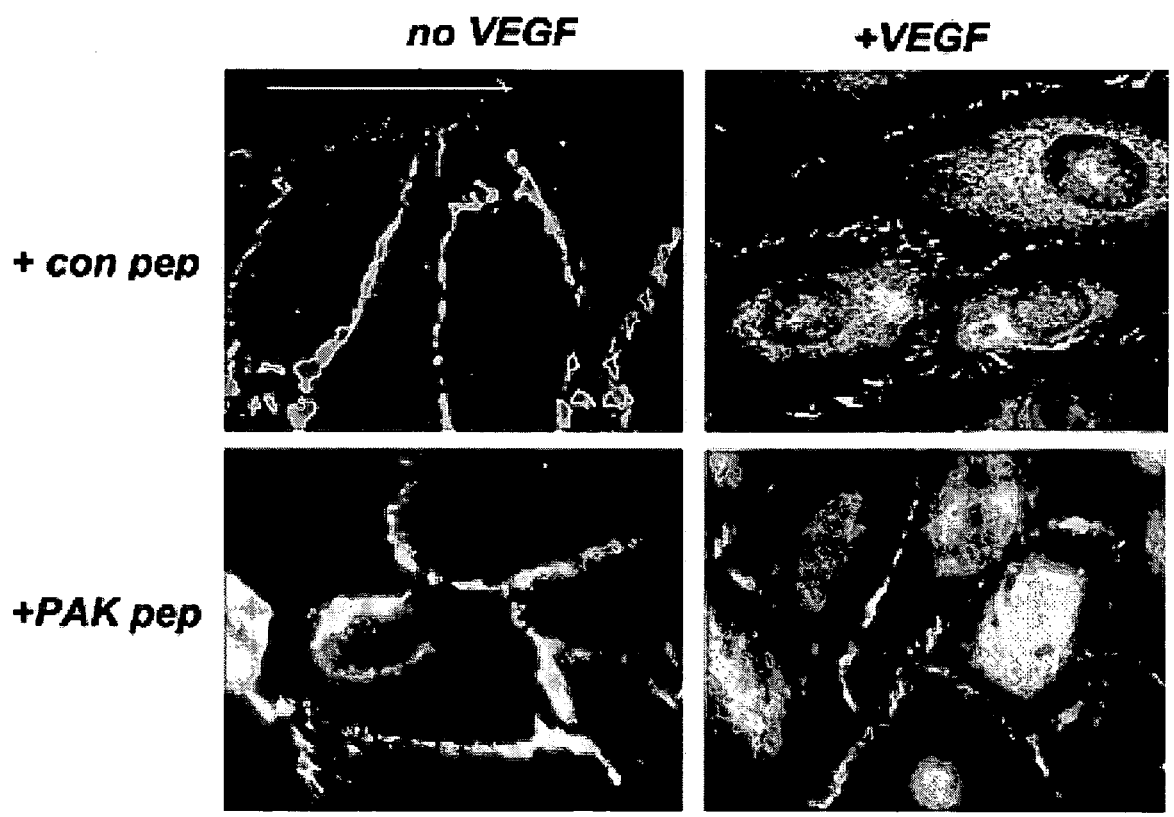
FIG. 7. Stabilization of adherens junctions. Confluent HUVEC on FN-coated coverslips were starved in medium with 0.5% serum for 18 hours, preincubated in 20 μg/ml control peptide (+con pep) or PAK-blocking peptide (+PAK pep) and then treated with (+VEGF) or without (no VEGF) 25 ng/ml VEGF for 60 min. The cells were fixed and stained for β-catenin. Scale bar=50μ.

Because permeability is controlled in part by adherens junctions, we also examined β-catenin distribution in VEGF-treated cells (FIG. 7). The addition of the PAK-blocking peptide to otherwise untreated cells appeared to thicken junctional staining of this marker compared with cells treated with the inactive control PAK peptide. The addition of VEGF decreased junctional integrity, inducing a shift to more broken staining along the cell-cell borders, as has been described (36, 41, 42). The PAK peptide largely prevented this VEGF-induced rearrangement, whereas the control peptide had no effect. Thus, changes in permeability correlate with effects on a junctional marker and support the notion that decreased tension in a subpopulation of cells can be transmitted to a wider region of the monolayer.

Example 8

Vascular Permeability in Mouse Lung Treated with Lipopolysaccharide (LPS) With or Without PAK-Blocking Peptide (PAK) or Inactive Control Peptide (PAK Control)

Methods:

Wild-type C57BL/6 mice were treated by intraperitoneal injection with 1.0 mg/mouse with either no peptide, a control inactive PAK peptide (Pak control) or with the Pak function-blocking peptide (PAK) for 60 minutes. Mice were then treated intraperitoneally with 10 mg/kg of LPS for 6 hours. Anaesthetized mice (1.0 mg/ml ketamine by injection) received an intravenous injection of Evans blue dye (30 mg/kg) for 30 minutes. Mice were killed and broncheoalveolar lavage (BAL) fluid was obtained by lavage with 2.25 ml of PBS with 1 mM EDTA (0.75 ml×3) through a 22-gauge intravenous cannula. The BAL fluid was centrifuged at 500×g for 5 minutes, and the supernatants were retained for evaluation of Evans blue dye extravasation from circulation as assessed by spectrophotometry of the supernatants at 610 nm.

Figure 8:
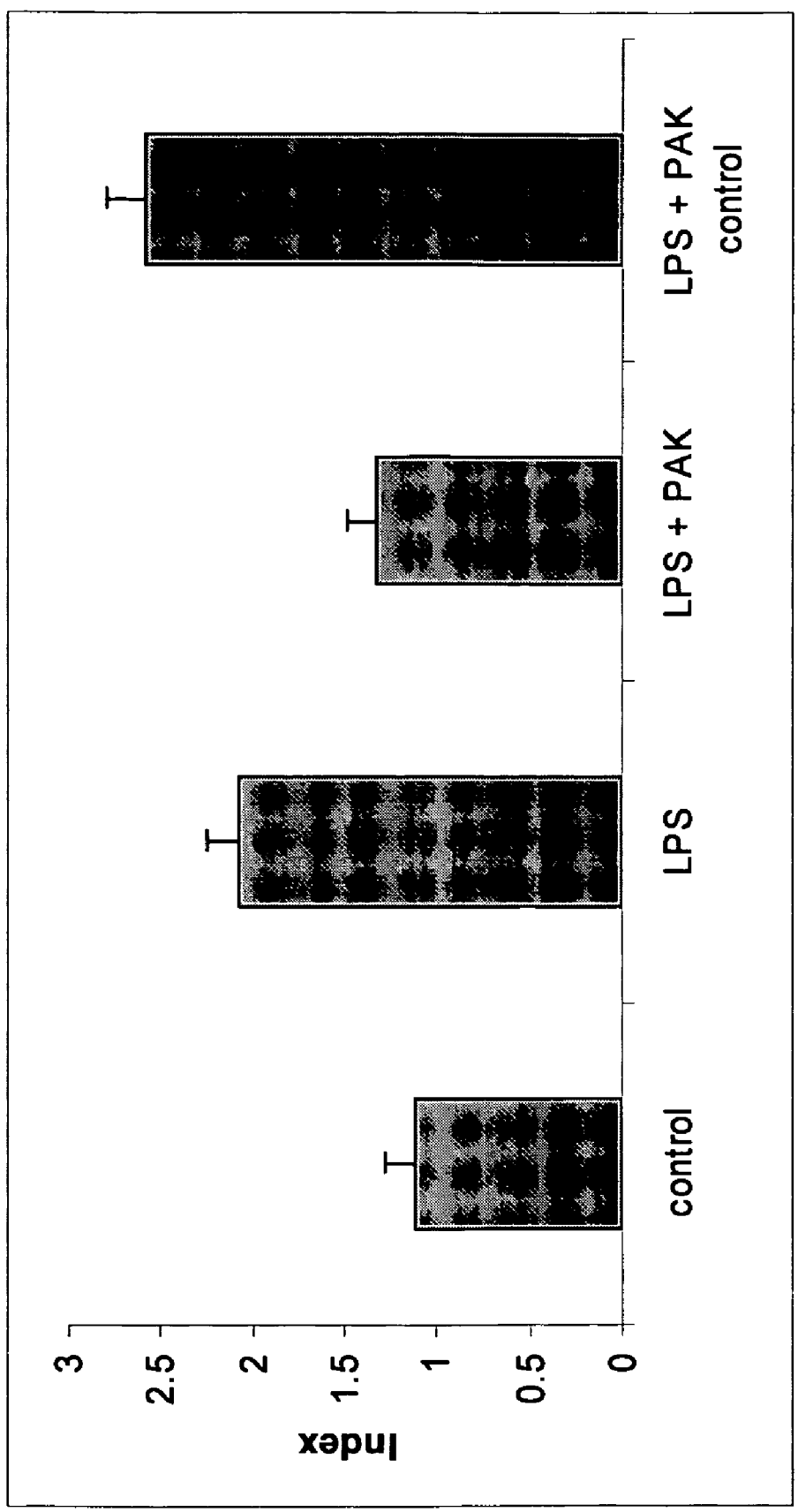
FIG. 8. Vascular permeability in mouse lung treated with lipopolysaccharide (LPS) with or without PAK-blocking peptide (PAK) or inactive control peptide (PAK control). "Index" (y-axis) refers to amount of Evans Blue dye leaked from pulmonary circulation into bronchiolar exudates and retrieved by bronchiolar lavage (BAL). Bars indicate means and standard errors of data from three experiments. "LPS" only and "LPS+PAK control" are statistically greater than control ($p<0.001$); while "LPS+PAK" (blocking peptide) is significantly less than LPS-only (p<0.001) and statistically equivalent to control (p<0.05).

Results:

FIG. 8 is a graphic illustration of the Evans Blue absorbance index as a function of relative pulmonary vascular permeability. Evans blue dye binds tightly to blood serum albumin, a large protein. Appearance of the dye in the mouse's BAL is a means of evaluating protein leak from circulation, across the blood vessel endothelial barrier into surrounding spaces. The absorbance measurement of the dye content is a linear assay and so the numbers are meaningfully quantitative. It can be seen in FIG. 9 that untreated mice (control) demonstrate the amount of basal leak that would be expected in normal circumstances. Addition of LPS (+LPS), a known inducer of vascular leak, increases the Evans Blue index two-fold over control untreated mice, meaning that twice as much protein leaks across the pulmonary endothelium after exposure to LPS. LPS treatment in mice pretreated with the inactive control peptide (LPS+PAK control) induces approximately the same amount of leak as LPS-only mice, since the peptide is inert and does not influence PAK. LPS treatment of mice pre-treated with the active PAK-blocking peptide (LPS+PAK) results in a significant reduction in pulmonary vascular leak to near-equivalence with control mice. These data indicate that prevention of PAK intracellular translocation with the blocking peptide effectively limits pulmonary endothelial cell retraction in response to LPS in vivo. This prevents leak of serum and proteins across the endothelial barrier even in the presence of a highly inflammatory leak-inducing compound.

Example 9

Histology of Murine Lungs Treated With PAK Blocking Peptide and LPS Methods

Mice were treated with either inactive control or PAK-blocking peptide (1 mg/animal; intraperitoneal). Then LPS (10 mg/kg) was administered for 6 hours. The animals were anesthetized and then the lungs were removed, frozen and paraffin-embedded. Cross-section slides were acquired by microtome and affixed to glass slides. Slides were deparaffinized, rehydrated, blocked, and probed with rabbit anti-pPAK $S^{141}$ or anti-pERK polyclonal Ab (1:500) 8 hours at 40° C. Slides were washed and stained with goat anti-rabbit IgG coupled to peroxidase, incubated with peroxide substrate, dehydrated, and sealed. The slides were then examined and photographed digitally on an Olympus BH-2 microscope using bright-field visualization. Image acquisition and processing was performed with ImageProPlus software.

Figure 9A:
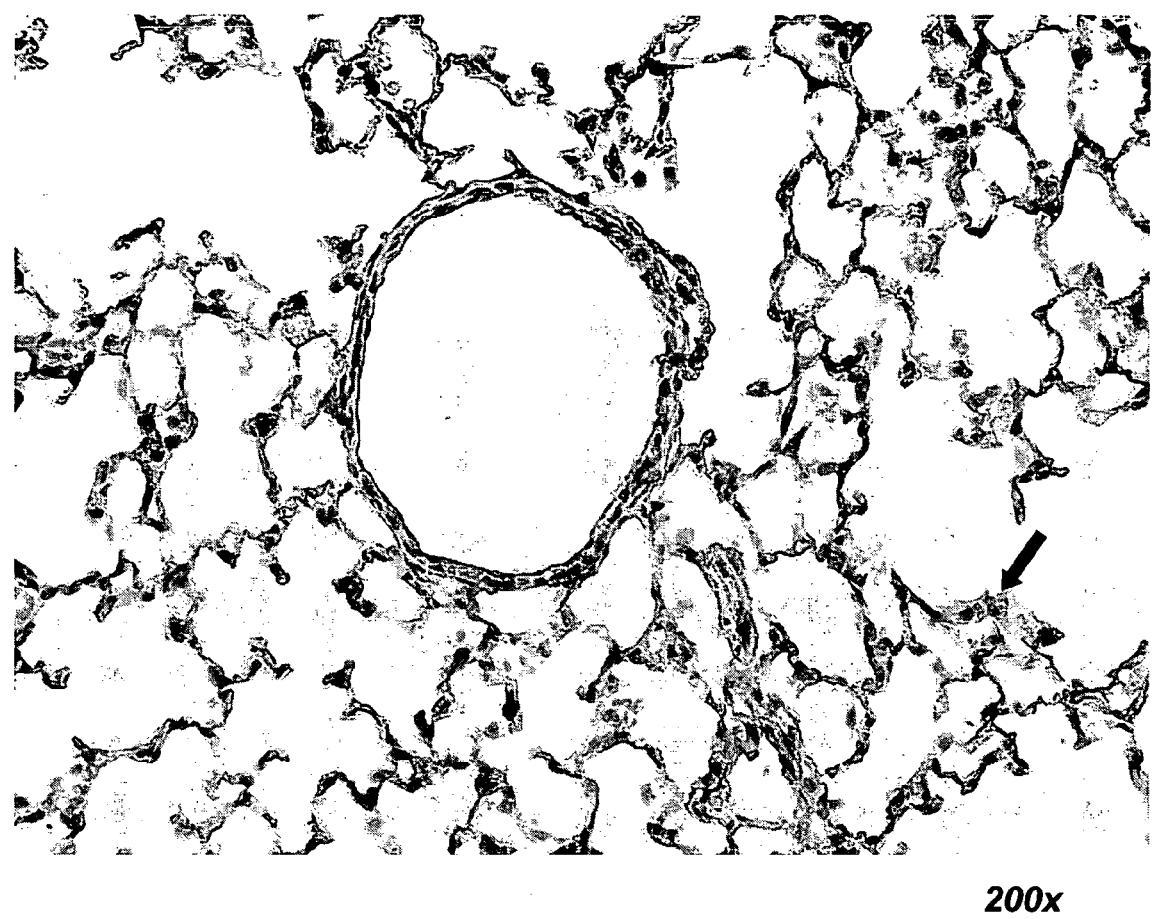
FIGS. 9A (200× magnification), 9B (400×), and 9C (200×) represent photomicrographic images. Pulmonary tissue in mice treated with peptide-only are equivalent to untreated mice, and demonstrate normal intact alveolar structures and blood vessels, with no evidence of inflammation. There is some phosphoPAK staining (visible as brown stain in the original color micrographs) present in epithelial structures, alveolar walls (composed of mixed cell types), and vessel endothelium and smooth muscle. Arrow indicates a normal small vessel with red blood cells and few circulating leukocytes. Tissues were counterstained with hematoxylin.
Figure 9B:
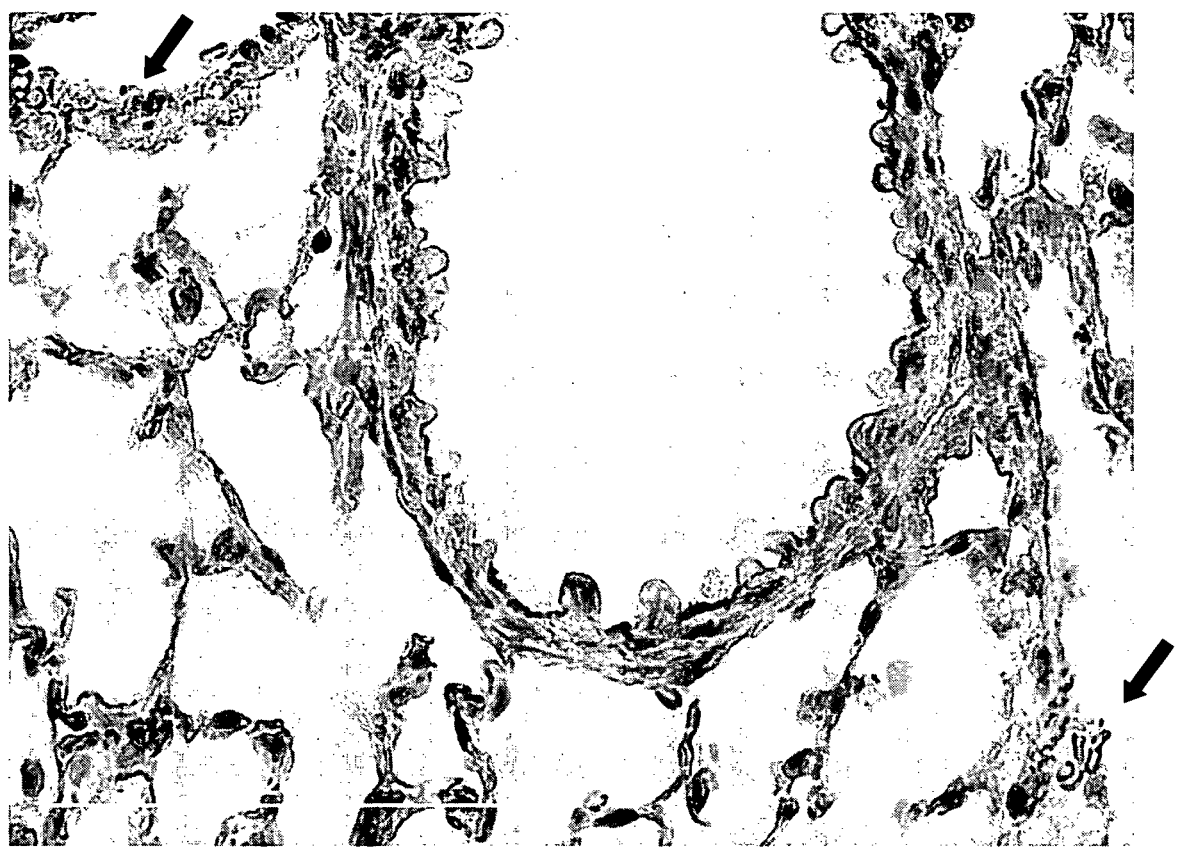
FIG. 9. Histology of murine lungs treated with PAK blocking peptide and LPS.
Figure 9C:
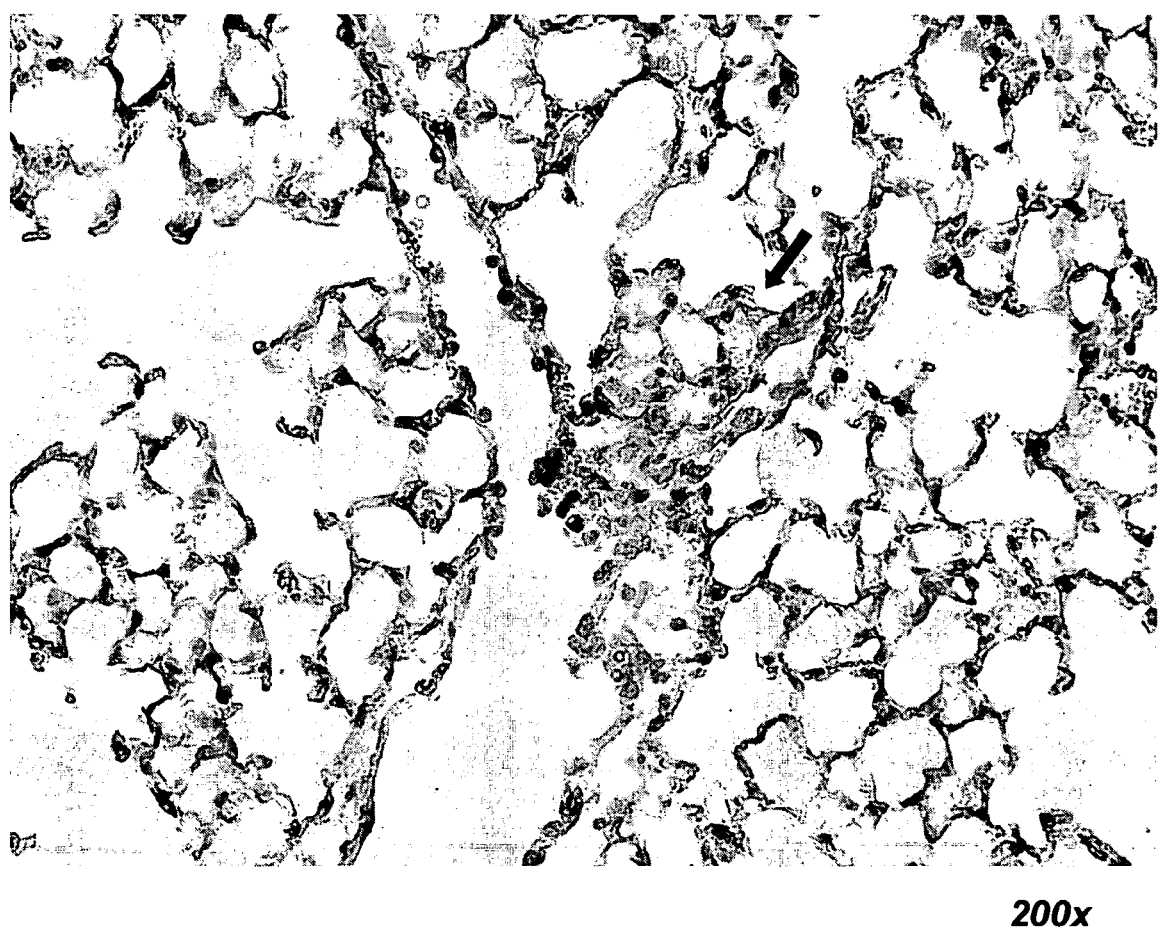

Results:

The results are depicted in the micrographs of FIGS. 9, 10, and 11. Mouse lung treated with LPS plus the control inactive peptide shows PAK activation, extensive leukocyte infiltration, and filling of alveolar space. The PAK inhibitor peptide blocks these events, lung tissue looks like normal tissue without LPS.

FIG. 9 demonstrates histologically that pulmonary tissue in mice treated with peptide-only (1 mg ip) is equivalent to pulmonary tissue in untreated mice, and demonstrates normal intact alveolar structures and blood vessels, with no evidence of inflammation. There is some phosphoPAK (indicated by brown stain in color micrographs which are not presented here) present in epithelial structures, alveolar walls (composed of mixed cell types), and vessel endothelium and smooth muscle. Arrows indicates a normal small vessel with red blood cells and few circulating leukocytes. The alveolar spaces are clear with few leukocytes. The blood vessels have few leukocytes.

Figure 10B:
FIG. 10. Histology of murine lungs treated with PAK blocking peptide and LPS.
FIGS. 10A (200× magnification), 10B (400×), and 10C (200×) represent photomicrographic images. Treatment with an inert control peptide plus LPS induces PAK activation by phosphorylation (depicted as brown stain in original color micrograph) in many pulmonary tissues, particularly vessel endothelium, epithelial tract lining, and smooth muscle. Vessel sections (arrow) indicate that LPS highly increases the amount of pPAK in vessel walls, and also produces inflammatory enlargement of vessels, with an increase in numbers of recruited neutrophils and monocytes admixed with red blood cells and intravasating through vessel walls, an indicator of acute inflammation. Some alveolar tissues are completely eroded and filled with exudate and dead cells (FIG. 10C). Tissues were counterstained with hematoxylin.
Figure 10A:
Figure 10C:
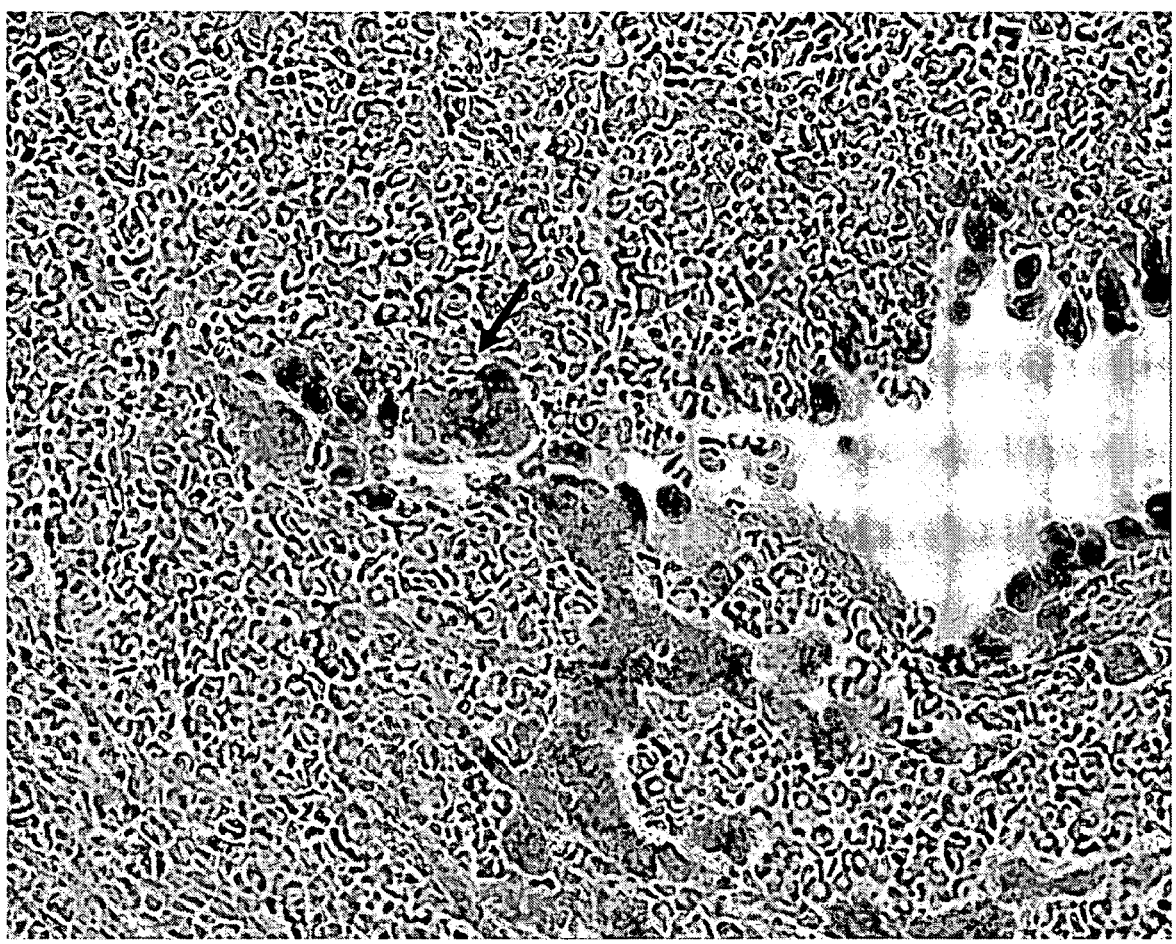

FIG. 10, comprising FIGS. 10A to 10C, demonstrates histologically that treatment with an inert control peptide (1 mg ip) plus LPS (10 mg/kg hrs) induces PAK activation by phosphorylation (brown stain in original color micrograph) in many pulmonary tissues, particularly vessel endothelium, epithelial tract lining and smooth muscle. Vessel sections (arrow) indicate that LPS treatment greatly increases the amount of pPAK in vessel walls, and also produces inflammatory enlargement of vessels, with an increase in numbers of recruited neutrophils and monocytes admixed with red blood cells and intravasating through vessel walls, an indicator of acute inflammation. There is evidence of increased monocyte adherence to epithelium. Some alveolar tissues are completely eroded and filled with exudate and dead cells (FIG. 10C).

Figure 11A:
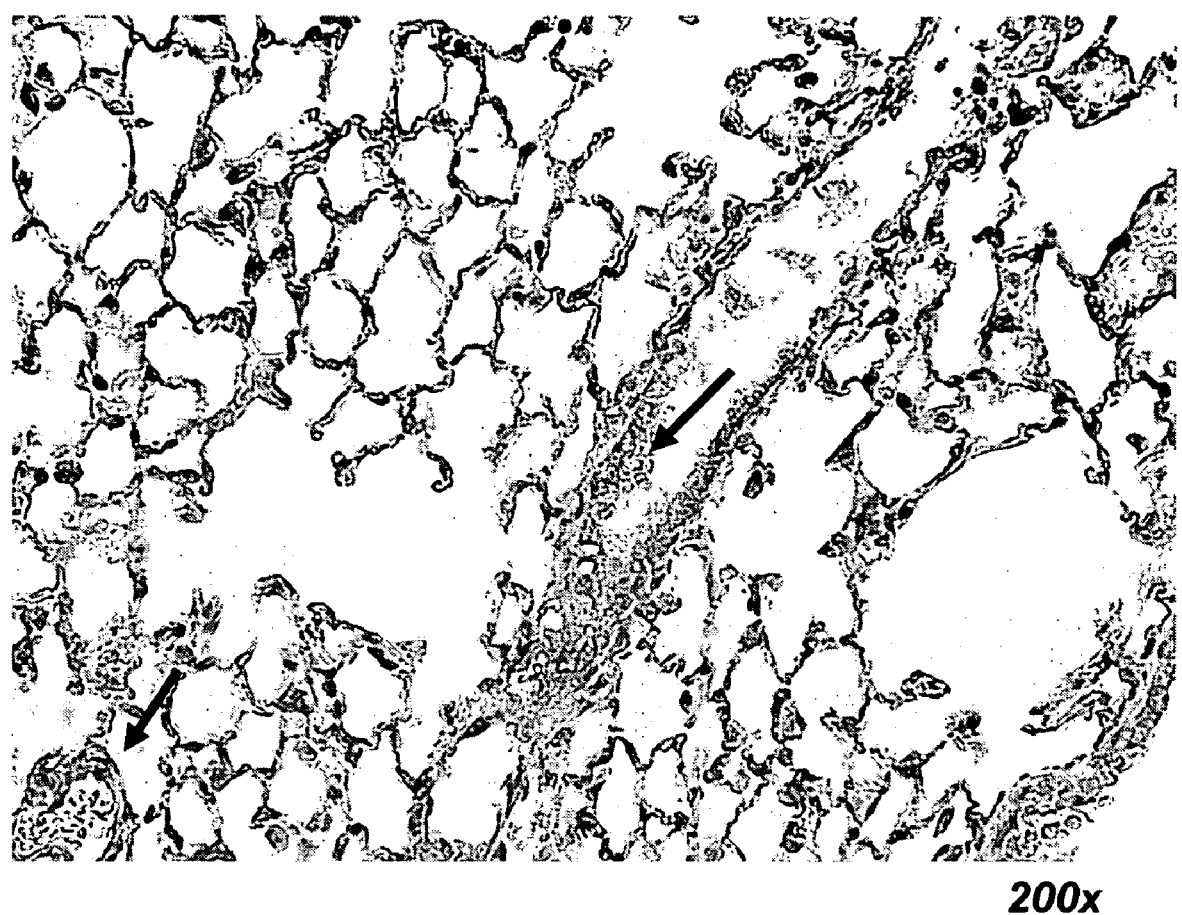
FIGS. 11A (200× magnification), 11B (400×), and 11C (200×) represent photomicrographic images. Mice co-treated with the PAK function-blocking peptide and LPS show nearly-normal pulmonary morphology. Inflammatory recruitment of leukocytes is diminished, and vessels show little thickening from inflammation (arrows). Alveolar structures are normal and intact. Tissues were counterstained with hematoxylin.
Figure 11B:
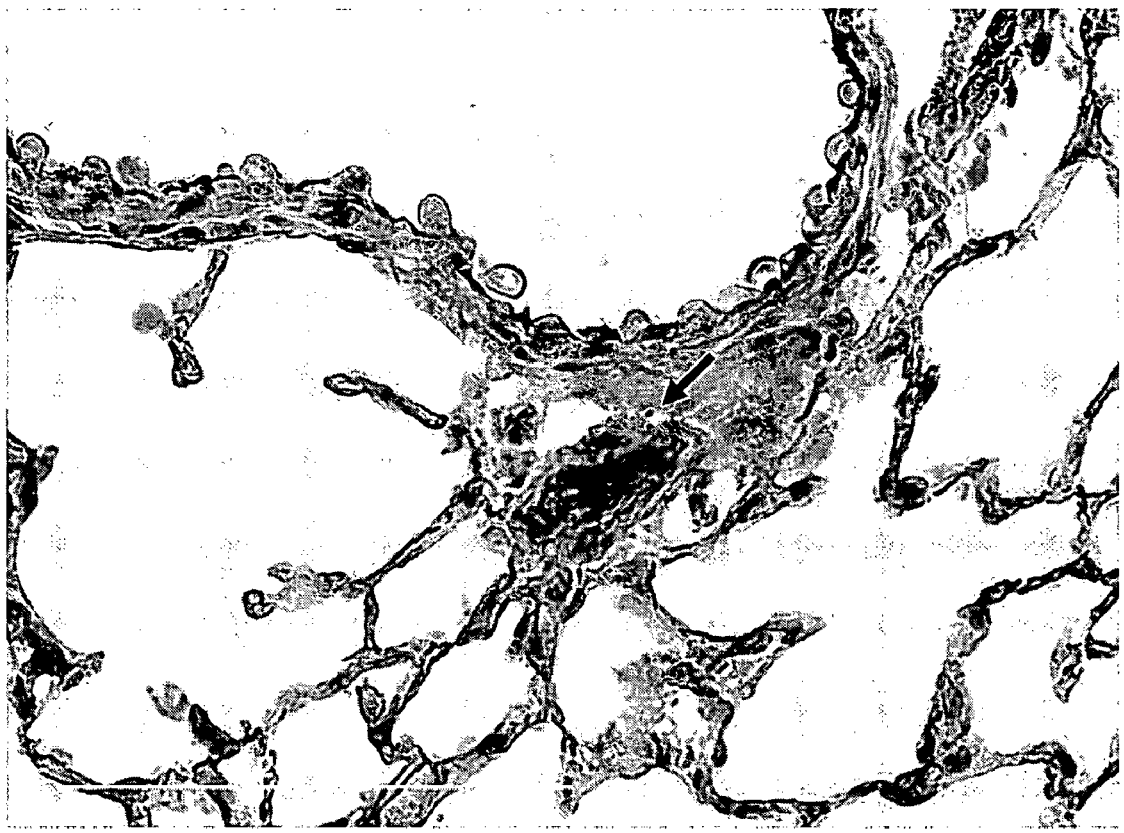
FIG. 11. Histology of murine lungs treated with PAK blocking peptide and LPS.
Figure 11C:

FIG. 11, comprising FIGS. 11A to 11C, demonstrates histologically that mice co-treated with the PAK function-blocking peptide (1 mg ip) and LPS (10 mg/kg 6 hours) show nearly-normal pulmonary morphology. Inflammatory recruitment of leukocytes is diminished, and vessels show little thickening from inflammation (arrows). Alveolar structures are normal and intact.

Without wishing to be bound by any particular theory, it is hypothesized that these data indicate that PAK is a central regulator of cell-cell contacts between endothelial cells. The PAK-blocking peptide prevents phosphorylated active PAK from localizing to the cell-cell junctions, and thereby prevents these cells lining the vessel walls from contracting and separating. Furthermore, vessel integrity is maintained even in the presence of a highly inflammatory agent, LPS.

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. The appended claims are intended to be construed to include all such embodiments and equivalent variations. Accordingly, the present invention is not intended to be limited to the embodiments shown herein but is to be accorded the widest scope consistent with the principles and novel features disclosed herein.

PERTINENT REFERENCES

1. Suzuki et al., Int. J. Biochem. Cell Biol., 2003, 35:881-900.
2. Dudek et al., J. Appl. Physiol., 2001, 91:1487-1500.
3. van Nieuw Amerongen et al., Vascul. Pharmacol., 2002, 39:257-272.
4. Paul et al., Nat. Med., 2001, 7:222-227.
5. Weis et al., J. Clin. Investig., 2004, 113:885-894.
6. Bogatcheva et al., Biochemistry (Mosc.), 2002, 67:75-84.
7. Lee et al., Microsc. Res. Tech., 2003, 60:115-127.
8. Takaishi et al., J. Cell Biol., 1997, 139:1047-1059.
9. Ridley et al., Mol. Cell. Biol., 1995, 15:1110-1122.
10. Hordijk et al., Science, 1997, 278:1464-1466.
11. Wojciak-Stothard et al., Vascul. Pharmacol., 2002, 39:187-199.
12. Eriksson et al., Circulation, 2003, 107:1532-1538.
13. Bokoch et al., Annu. Rev. Biochem., 2003, 72:743-781.
14. Zenke et al., J. Biol. Chem., 1999, 274:32565-32573.
15. Sells et al., J. Cell Biol., 2000, 151:1449-1458.
16. Gatti et al., J. Biol. Chem., 1999, 274, 8022-8028.
17. Edwards et al., Nat. Cell Biol., 1999, 1, 253-259.
18. Chew et al., J. Muscle Res. Cell Motil., 1998, 19:839-854.
19. Goeckeler et al., J. Biol. Chem., 2000, 275:18366-18374.
20. Zeng et al., J. Cell Sci., 2000, 113:471-482.
21. Sanders et al., Science, 1999, 283:2083-2085.
22. Wirth et al., J. Physiol. (Lond), 2003, 549:489-500.
23. Kiosses et al., J. Cell Biol., 1999, 147:831-844.

24. Katsumi et al., J. Cell Biol., 2002, 158:153-164.
25. del Pozo et al., EMBO J., 2000, 19:2008-2014.
26. Kiosses et al., Circ. Res., 2002, 90:697-702.
27. Chong et al., J. Biol. Chem., 2001, 276:17347-17353.
28. Hood et al., J. Cell Biol., 2003, 162:933-943.
29. Garcia et al., J. Cell. Physiol., 1995, 163:510-522.
30. Valeski et al., Microcirculation, 2003, 10:411-420.
31. Watanabe et al., FASEB J., 1998, 12:341-348.
32. Yuan et al., Circ. Res., 2002, 90:1214-1221.
33. Sells et al., J. Cell Biol., 1999, 145:837-849.
34. Rudrabhatla et al., Infect. Immun., 2003, 71:2787-2797.
35. Bisson et al., Dev. Biol., 2003, 263:264-281.
36. Esser et al., J. Cell Sci., 1998, 111:1853-1865.
37. Birukov et al., Am. J. Respir. Cell Mol. Biol., 2002, 26:453-464.
38. Lampugnani et al., Mol. Biol. Cell, 2002, 13:1175-1189.
39. Becker et al., Am. J. Physiol., 2001, 281:L1500-L1511.
40. Kiosses et al., J. Cell Biol., 1999, 147:831-844.
41. Wang et al., Am. J. Physiol., 2001, 280:H434-H440.
42. Antonetti et al., J. Biol. Chem., 1999, 274:23463-23467.
43. Sells et al., J. Cell Biol., 1999, 145:837-849.
44. Dudek et al., J. Appl. Physiol., 2001, 91:1487-1500.
45. Essler et al., J. Biol. Chem., 1998, 273:21867-21874.
46. Stevens et al., Am. J. Physiol., 2000, 279:L419-L422.
47. Noritake et al., Mol. Biol. Cell, 2004, 15:1065-1076.
48. Zhou et al., J. Biol. Chem., 1998, 273:16782-16786.
49. Buchsbaum et al., Mol. Cell. Biol., 2002, 22:4073-4085.
50. Buchsbaum et al., J. Biol. Chem., 2003, 278:18833-18841.
51. Groeneveld, Vascul. Pharmacol., 2002, 39:247-256.
52. Lush et al., Microcirculation, 2000, 7:83-101.
53. Stockton et al., J. Biol. Chem., 2004, 279:45:46621-46630.

SEQUENCE LISTING

```
<160> NUMBER OF SEQ ID NOS: 3

<210> SEQ ID NO 1
<211> LENGTH: 25
<212> TYPE: PRT
<213> ORGANISM: Unknown
<220> FEATURE:
<223> OTHER INFORMATION: The sequence is a hybrid peptide comprising a
      combination of the human peptide of SEQ ID NO:2 and the HIV
      peptide of SEQ ID NO:3.

<400> SEQUENCE: 1

Tyr Gly Arg Lys Lys Arg Arg Gln Arg Arg Gly Lys Pro Pro Ala
1               5                   10                  15

Pro Pro Met Arg Asn Thr Ser Thr Met
            20                  25

<210> SEQ ID NO 2
<211> LENGTH: 13
<212> TYPE: PRT
<213> ORGANISM: homo sapiens

<400> SEQUENCE: 2

Lys Pro Pro Ala Pro Pro Met Arg Asn Thr Ser Thr Met
1               5                   10

<210> SEQ ID NO 3
<211> LENGTH: 12
<212> TYPE: PRT
<213> ORGANISM: Human immunodeficiency virus

<400> SEQUENCE: 3

Tyr Gly Arg Lys Lys Arg Arg Gln Arg Arg Arg Gly
1               5                   10
```

What is claimed is:

1. A method of therapeutically treating a vascular permeability associated disease or disorder in a subject in need thereof, said method comprising administering to said subject a pharmaceutical composition comprising an effective amount of at least one inhibitor of p21-activated kinase and a pharmaceutically-acceptable carrier, so as to inhibit said vascular permeability and alleviate said disease or disorder.

2. The method of claim 1, wherein said inhibitor regulates endothelial cell permeability.

3. The method of claim 1, wherein said inhibitor of p-21 activated kinase inhibits translocation of p21-activated kinase.

4. The method of claim 1, wherein said inhibitor of p21-activated kinase inhibits growth-factor stimulated vascular permeability.

5. The method of claim 1, wherein said inhibitor of p21-activated kinase inhibits cytokine stimulated vascular permeability.

6. The method of claim 1, wherein said inhibitor of p21-activated kinase inhibits bacterial toxin stimulated vascular permeability.

7. The method of claim 1, wherein said subject has a vascular permeability associated disease or disorder, selected from the group consisting of acute respiratory distress syndrome, ischemia, inflammation, stroke, wound healing, hypertension, myocardial infarction, sepsis, hypoxia, infection, allergic reaction, thermal injury, and damage due to x-irradiation or ultraviolet irradiation.

8. The method of claim 1, wherein said inhibitor of p21-activated kinase inhibits endothelial cell p21-activated kinase.

9. The method of claim 8, wherein said inhibitor of endothelial cell p21-activated kinase inhibits a vascular endothelial cell p21-activated kinase.

10. The method of claim 1, wherein said inhibitor of p21-activated kinase inhibits activation of p21-activated kinase.

11. The method of claim 10, wherein said inhibitor of p21-activated kinase inhibits binding of a protein with p21-activated kinase.

12. The method of claim 1, wherein said inhibitor of p21-activated kinase is a peptide.

13. The method of claim 12, wherein said inhibitor of p21-activated kinase is a peptide comprising an amino acid sequence selected from the group consisting of SEQ ID NO:1 and SEQ ID NO:2, or a biologically active fragment, homolog, or derivative thereof.

14. The method of claim 13, wherein said peptide has at least about 70% sequence identity with SEQ ID NO:1, or a biologically active fragment, homolog, or derivative thereof.

15. The method of claim 14, wherein said peptide has at least about 90% sequence identity with SEQ ID NO:1, or a biologically active fragment, homolog, or derivative thereof.

16. The method of claim 15, wherein said peptide has at least about 95% sequence identity with SEQ ID NO:1, or a biologically active fragment, homolog, or derivative thereof.

17. The method of claim 13, wherein said peptide has at least about 70% sequence identity with SEQ ID NO:2, or a biologically active fragment, homolog, or derivative thereof.

18. The method of claim 17, wherein said peptide has at least about 90% sequence identity with SEQ ID NO:2, or a biologically active fragment, homolog, or derivative thereof.

19. The method of claim 18, wherein said peptide has at least about 95% sequence identity with SEQ ID NO:2, or a biologically active fragment, homolog, or derivative thereof.

* * * * *